(12) United States Patent
Domb et al.

(10) Patent No.: US 8,535,645 B2
(45) Date of Patent: Sep. 17, 2013

(54) ANTIMICROBIAL NANOPARTICULATE ADDITIVES FORMING NON-LEACHABLE SUSTAINED ANTIMICROBIAL POLYMERIC COMPOSITIONS

(75) Inventors: Abraham J. Domb, Efrat (IL); Ervin Weiss, Herzeliya (IL); Nurit Beyth, Jerusalem (IL); Ira Farber, Nazaret Elit (IL); Michael Perez Davidi, Savion (IL)

(73) Assignees: Hadasit Medical Research Services & Development Limited, Jerusalem (IL); Yissum Research Development Company of the Hebrew University of Jerusalem, Jerusalem (IL)

( * ) Notice: Subject to any disclaimer, the term of this patent is extended or adjusted under 35 U.S.C. 154(b) by 382 days.

(21) Appl. No.: 11/794,492

(22) PCT Filed: Jan. 1, 2006

(86) PCT No.: PCT/IL2006/000005
§ 371 (c)(1),
(2), (4) Date: Oct. 1, 2007

(87) PCT Pub. No.: WO2006/070376
PCT Pub. Date: Jul. 6, 2006

(65) Prior Publication Data
US 2008/0226728 A1 Sep. 18, 2008

Related U.S. Application Data

(60) Provisional application No. 60/639,966, filed on Dec. 30, 2004.

(51) Int. Cl.
*A61K 8/00* (2006.01)
*A61K 9/14* (2006.01)
*C11D 1/62* (2006.01)

(52) U.S. Cl.
USPC ........ 424/49; 424/9.322; 424/70.28; 424/489

(58) Field of Classification Search
USPC .............................. 424/49, 9.322, 70.28, 489
See application file for complete search history.

(56) References Cited

U.S. PATENT DOCUMENTS

| | | | |
|---|---|---|---|
| 5,408,022 A | 4/1995 | Imazato et al. | |
| 5,494,987 A | 2/1996 | Imazato et al. | |
| 5,672,638 A * | 9/1997 | Verhoeven et al. | 523/112 |
| 5,733,949 A | 3/1998 | Imazato et al. | |
| 5,798,117 A | 8/1998 | New et al. | |
| 5,980,868 A * | 11/1999 | Homola et al. | 424/54 |
| 6,039,940 A * | 3/2000 | Perrault et al. | 424/78.06 |
| 6,559,116 B1 | 5/2003 | Godfroid et al. | |
| 6,562,330 B1 | 5/2003 | Stratford et al. | |
| 2004/0180093 A1* | 9/2004 | Burton et al. | 424/489 |
| 2005/0277752 A1 | 12/2005 | Bringley | |

FOREIGN PATENT DOCUMENTS

| | | |
|---|---|---|
| WO | WO 93/20775 | 10/1993 |
| WO | WO 9320775 A1 * | 10/1993 |
| WO | 2005/123612 A2 | 12/2005 |

OTHER PUBLICATIONS

J Lin, S Qiu, K Lewis, AM Klibanov. "Mechanism of Bactericidal and Fungicidal Activities of Textiles Covalently Modified With Alkylated Polyethylenimine." Biotechnology and Bioengineering, vol. 83, No. 2, July 20, 2003. pp. 168-172.*

J Lin, S Qiu, K Lewis, Am Klibanov. "Bactericidal Properties of Flat Surfaces and Nanoparticles Derivatized with Alkylated Polyethylenimines." Biotechnol. Prog., vol. 18, 2002, pp. 1082-1086.*

Lin, Jian, et al., "Bactericidal Properties of Flat Surfaces and Nanoparticles Derivatized with Alkylated Polyethylenimines," *Biotechnol. Prog.*, vol. 18 pp. 1082-1086, (2002).

Kawabata, Nariyoshi, et al., "Antibacterial Activity of Soluble Pyridinium-Type Polymers," *Applied and Environmental Microbiology*, vol. 54, No. 10, pp. 2532-2535, (1988).

Imazato, S., et al., "Cytotoxic effects of composite restorations employing self-etching primers or experimental antibacterial primers," *Journal of Dentistry*, vol. 28, pp. 61-67, (2000).

Imazato, S., et al., "Penetration of an antibacterial dentine-bonding system into demineralized human root dentine in vitro," *European Journal of Oral Sciences*, vol. 110, pp. 168-174 (2002).

Imazato, S., et al., "Antibacterial activity of bactericide-immobilized filler for resin-based restoratives," *Biomaterials*, vol. 24, pp. 3605-3609, (2003).

* cited by examiner

*Primary Examiner* — Lezah Roberts
*Assistant Examiner* — Tracy Liu
(74) *Attorney, Agent, or Firm* — Vorys, Sater, Seymour and Pease LLP; Susanne M. Hopkins

(57) ABSTRACT

A particle including at least one aliphatic polymer having anti-microbially active quaternary ammonium groups chemically bound thereto, is provided. The particle may be used to inhibit populations of microorganisms and biofilms. Also provided are methods for the preparation of such particles and uses thereof for the inhibition of microorganisms.

45 Claims, 4 Drawing Sheets

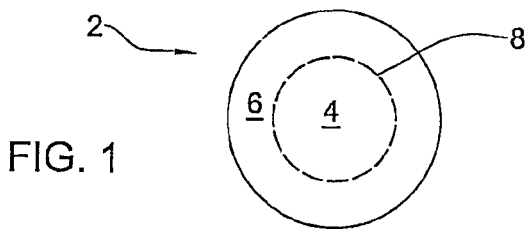
FIG. 1
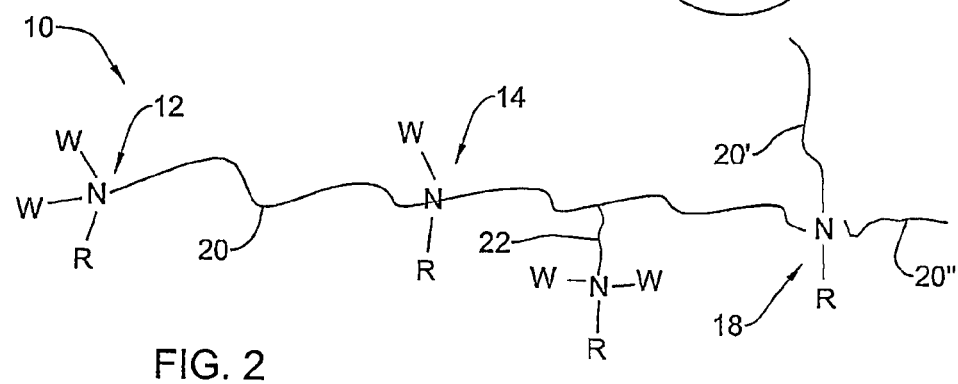
FIG. 2
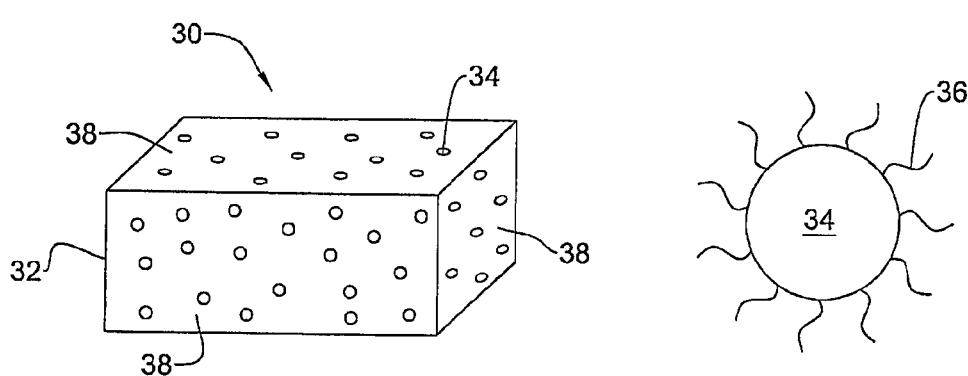
FIG. 3
FIG. 4
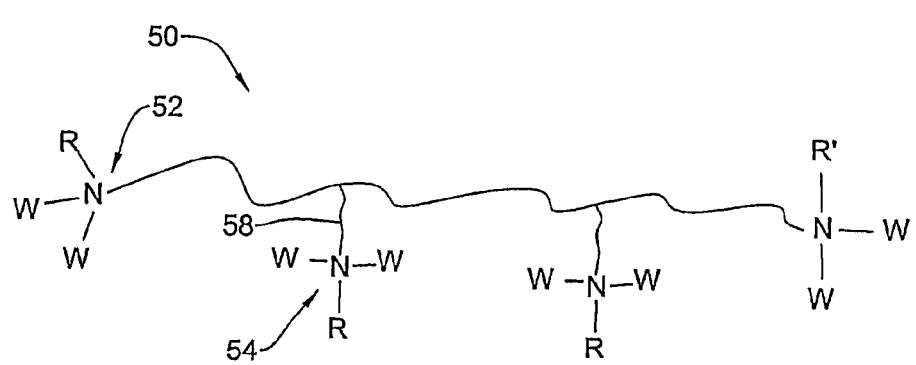
FIG. 5

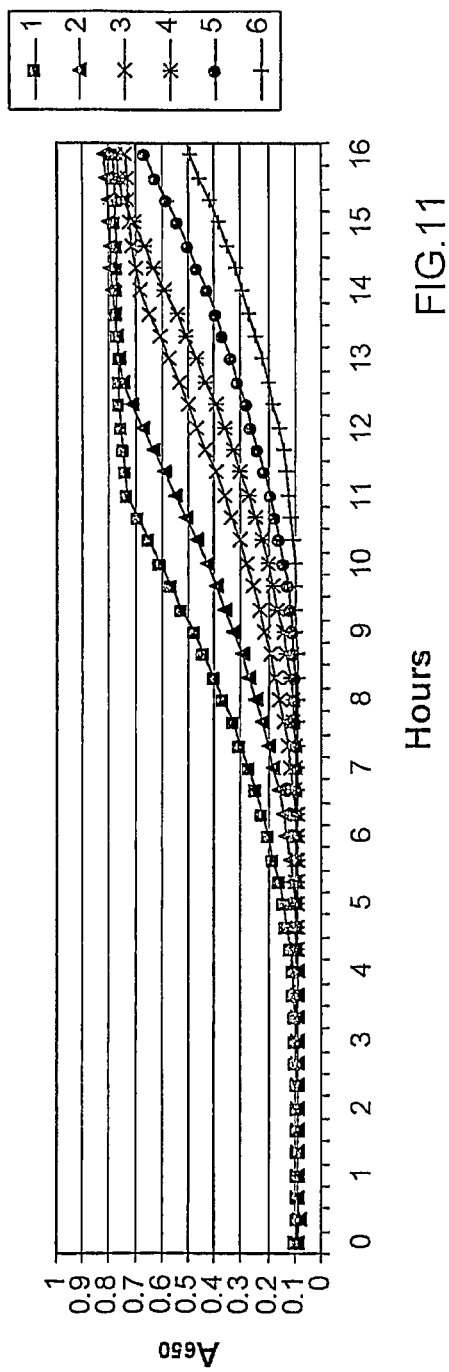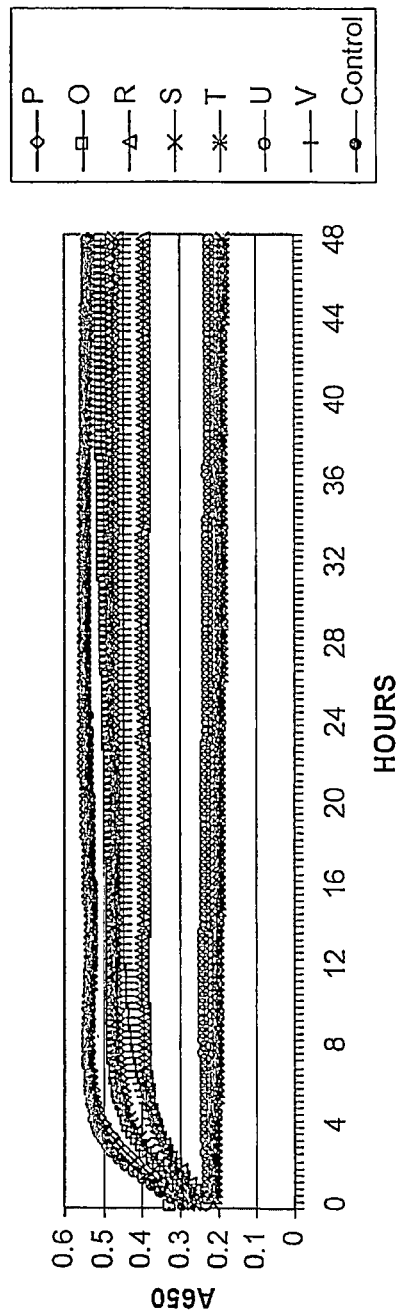

US 8,535,645 B2

ANTIMICROBIAL NANOPARTICULATE ADDITIVES FORMING NON-LEACHABLE SUSTAINED ANTIMICROBIAL POLYMERIC COMPOSITIONS

CROSS-REFERENCE

This is a National Phase Application filed under 35 U.S.C. 371 of International Application No. PCT/IL2006/000005, filed Jan. 1, 2006, claiming the benefit under 35 USC 119(e) of U.S. Provisional Application No. 60/639,966, filed Dec. 30, 2004, the entire contents of each of which is hereby incorporated herein by reference in its entirety.

FIELD OF THE INVENTION

This invention relates to antimicrobally active particles, matrices containing such particles, polymers useful for making such particles, methods of making such particles and methods for making such matrices.

BACKGROUND OF THE INVENTION

Antimicrobial surfaces have been a major challenge particularly in medicine where microbial agents tend to accumulate and propagate onto implantable devices made of various materials, particularly onto polymers. For example, indwelling catheters have to be removed sometimes shortly after administration due to accumulation of bacteria. For orthopedic implants such as artificial hips accumulation of bacteria may result in severe infection shortly or a few months after implant which in turn necessitates the removal of the implant an administration of high dose of antibacterial agents for healing before re-implantation. Urinary catheters may also result in a bladder infection from bacteria tracking through the catheter. Dental restoration material tend also to accumulate bacteria which result is deterioration of the restoration material while infecting the neighboring soft and hard tissues including the gums and dentin.

A number of reports describe experiments in which an antibacterial agent was incorporated into materials in order to inhibit bacterial growth. However, the antibacterial activity of these materials was found to be dependent upon release of the antibacterial agents into the surrounding milieu by various releasing rates.

U.S. Pat. No. 5,980,868 to Homola et al, describes dental coating of PEI reacted with a monolayer of fatty acid molecules, which fatty acids bond to the PEI layers with through their carboxylic groups. The invented material is said to be applied to dental surfaces by dental applicators including dental floss, tape, swabs and sticks. Published PCT Application No. WO 93/20775 introduces dental coating materials that contain particles of poly(fluoroetylene) coated with polyethyleneimine.

It has been reported that polycations possess antibacterial properties by interacting with and disrupting bacterial cell membranes. A number of polymers that exhibit antibacterial properties were developed for this purpose including soluble and insoluble pyridinium-type polymers which are involved in surface coating, azidated poly(vinyl chloride) which can be used to prevent bacterial adhesion of medical devices, PEG polymers that can be modified on polyurethane surfaces and also prevent initial adhesion bacteria to the biomaterial surfaces, and chitosans-polyethyleneimine that exhibit antibacterial and antifungal activity.

Numerous publications have demonstrated the utility of cationic polymers with quaternary ammonium groups as antimicrobial compounds. For example, U.S. Pat. No. 6,559,116 to Godfroid discloses antimicrobial composition for hard surface cleaning which consists of cationic antimicrobial active component which includes alkyltrimethylammonium halides and nitrogen-containing polymers such as polyethyleneimine. Lin et al (Lin J, Qiu S, Lewis K, Klibanov M. Bacterial properties of flat surfaces and nanoparticles derivatized with alkylated polyethylenimines. Biotechnol Prog 2002; 18:1082-1086) determined that covalently coated surfaces with N-alkylated poly(ethyleneimine) (PEI) may be effective against some airborne or waterborne Gram-positive and Gram-negative bacteria. Magnetoferic ($Fe_3O_4$) nanoparticles containing $NH_2$ groups and derivatized with alkylated polyethylenimines possess also antibacterial properties. The antibacterial activity was dependant on molecular weight of the conjugate. The results showed for example that N-alkylated PEI of 2 and 0.8 kDa had a weak bactericidal activity. High activity of polycationic agents, on the other hand, may be achieved by 750-25 kDa N-alkylated PEI.

The antibacterial action is suggested to result from absorption of positively charged polymers onto negatively charged cell surfaces of the bacteria. This process was thought to be responsible for the increase of cell permeability and disruption of cell membranes. (Kawabata N, Nishiguchi M. Antibacterial activity of soluble pyridinium-type polymers. Appl Environ Microbiol 1988; 54:2532-2535)

U.S. Pat. Nos. 5,733,949, 5,408,022, and 5,494,987 to Imazato et al disclose compositions comprising three polymerizable vinyl based monomers having a group with antimicrobial activity, a carboxylic acid group and a monomer having an hydroxyl group. The composition may possess effective antimicrobial activity due to the penetration properties of the carboxylic acid and hydroxyl groups into the bacteria cell. According to these patents the activity is declining after one month with the active compound leaching to the surroundings.

Imazato et al, (J. Dentisty 28. 2000, 61-67), discloses the use of 12-methacyloyloxydodecylpyridinium bromide (MDPB) as monomer in acrylate dental primers. In the course of the study it was found that the monomer does not contribute to the cytotoxicity to human pulpal cells. In an another article, (Eur. J. Oral Sci. 110, 2002, 168-174) Imazato reports on the use of three dentine-bonding agents containing MDPB for treating bacterial infections of the artificial root carries lesions and found it effective when incorporated as monomer in the bonding composition. Yet in another article (Biomaterials, 24. 2003, 3605-9) grinded polymerized MDPB exhibited strong anti S. mutans activity. In the study it was also found that unpolymerized monomer leach out from the grinded polymerized MDPB.

U.S. Pat. No. 5,798,117 to New at al. discloses surfaces having phosphatidyl choline (O—POO—$CH_2$—$CH_2$—N—$R_3$) derivatives capable of acting as antimicrobial surface. Similarly, U.S. Pat. No. 6,562,330 discloses certain compositions of antimicrobial materials based on zwiterioic functional groups such as phosphatidyl choline (O—POO—$CH_2$—$CH_2$—N—$R_3$) derivatives, amino acid derivatives and the like.

SUMMARY OF THE INVENTION

It has now been surprisingly found that nanoparticles comprising cationic polymers substituted with quaternary ammonium groups showed a broad spectrum of antimicrobial activity, e.g. antibacterial and antifungal activities when in contact with surfaces on which growth of such microbes may otherwise naturally take place. Such antimicrobial activity thus prevents for example biofilm formation. It was further determined that these nanoparticles maintain high antimicrobial properties over time without leaching out and with no alteration of the properties of the hosting matrix.

In one aspect of the invention there is provided a particle comprising at least one aliphatic polymer having anti-microbially active quaternary ammonium groups chemically bound thereto, and having at least one or a combination of the following characteristics:

1. the anti-microbially active quartarnary ammonium groups are at a surface density of at least one anti-microbially active quaternary ammonium group per sq. nm.;
2. said anti-microbially active quaternary ammonium groups amount to at least 10% of the amine groups in tie polymer;
3. said anti-microbially active quaternary ammonium group comprise one long alkyl group bound to the nitrogen atom.

In a one embodiment, said particle comprising at least one aliphatic polymer having anti-microbially active quaternary ammonium groups chemically bound thereto, said anti-microbially active quaternary ammonium group comprising one long alkyl group bound to the nitrogen atom. Preferably, the particle has a surface density of at least one anti-microbially active quaternary ammonium group per sq. nm.

In another embodiment, the particle has a surface density of at least one anti-microbially active quaternary ammonium group per sq. nm. Preferably, said particle comprising at least one aliphatic polymer having anti-microbially active quaternary ammonium groups chemically bound thereto, said anti-microbially active quaternary ammonium group comprising one long alkyl group bound to the nitrogen atom.

In yet another embodiment, said particle comprising at least one aliphatic polymer having anti-microbially active quaternary ammonium groups chemically bound thereto, and having a surface density of at least one anti-microbially active quaternary ammonium group per sq. nm, said anti-microbially active quaternary ammonium group comprising one long alkyl group bound to the nitrogen atom.

The at least one aliphatic polymer is selected from polyethylene imine (PEI), polyvinyl amine (PVA), poly(allyl amine) (PAA), poly(aminoethyl acrylate), aminomethylated styrene polymers, polypeptides with pending alkyl-amino groups, and chitosan.

The aliphatic polymer is preferably cross-linked. The degree of cross linking may be from 1% to 20%.

The particle of the invention may be between 10 to 10,000 nm in size. Preferably, it is at between 30 and 150 nm in size.

In another embodiment, at least 10% of the amine groups in the polymer making the particle of the invention are said anti-microbially active quaternary ammonium groups. The particle of the invention may further contain functional groups that are capable of reacting with a host polymer or with monomers thereof, to allow the particles to be bound chemically to the host polymer.

The particle according to the present invention may be embedded in a liquid or solid medium. Preferably said medium is a polymeric matrix.

According to another aspect of the invention, there is provided a polymeric matrix comprising a polymeric host embedding particles of the invention. The particles of the invention are preferably homogeneously distributed on the outer surface of the matrix in a surface concentration of between about 1 to about 100 particles per sq. μm.

In a preferred embodiment, the polymeric matrix of the invention has, on average, at least one active portion per sq. μm of outer surface of matrix, the size of such active portion is at least 100 nm$^2$; said active portion has surface concentration of at least 1 anti-microbially active quaternary amine per sq. nm. Preferably, the polymeric particles of the invention are chemically bound to the polymeric matrix.

In yet another aspect of the invention there is provided a method for inhibition, e.g. annihilation, of biological species, e.g. bacteria, parasites, fungi or viruses, by contacting said biological species with a polymeric matrix of the invention.

The polymers for use in the present invention are those having quaternary ammonium groups consisting of a nitrogen atom having only one bond to said polymer and three bonds to non-polymeric groups, one of which non-polymeric groups being an alkyl chain with four or more carbon atoms. In a preferred embodiment, at least 90% of said quaternary ammonium groups are anti-microbially active and one or more of the non-polymeric group which is not said alkyl with 4 or more carbon atoms is a short alkyl group with 3 or less carbon atoms, e.g. a methyl group.

Such polymers may be obtained by (a) providing a polymer with primary amine groups, (b) selectively substituting one hydrogen atom on each primary amine with an alkyl group comprising at least 4 carbon atoms; and (c) substituting the other aminic hydrogen atoms (if present) with short alkyl groups having 1, 2, or 3 carbon atoms.

The resulting polymers, as well as any other aliphatic polymenr of the invention which is obtained by any other synthetic or commercial way, may be embedded in a host, thus furnishing a polymeric matrix. The method for the production of such matrix comprises adding to a host polymer a surface active compound and particles according to the invention and mixing to obtain a homogeneous polymeric matrix. In such a method a compatabilizer may be used.

DETAILED DESCRIPTION OF THE INVENTION

The Nanoparticles

The polymeric particle has an inner portion and an outer portion which are continuous and homogenous. The inner and outer portions of a particle according to the invention are made of substantially the same compound, such that the inner portion cannot be dissociated from the outer portion, as the two portions are continuous and integral with each other.

The polymeric particle of the invention is 10-10,000 nm in size. Preferred are particles less than 1,000 nm in size, and most preferred are particles of up to 150 nm in size. Particles of more than 30 nm in size are also preferred. The size of a particle is given in terms of its diameter—if the particle is spherical, or in equivalent terms, in case the particle is not spherical. Equivalent terms may be the average of the length of the main axes of the particle, or the third root of its volume.

Preferably, the aliphatic polymer is cross-linked.

Crosslinking, as may be known to a person skilled in the art of organic synthesis and polymer science, may be affected by various agents and reactions that are per se known in the art. For example, crossliking may be affected by alkylating the polymer chains with dihaloalkane such as dibromoethane, dibromocyclohexane, or bis-bromomethylbenzene.

Alternatively, crosslinking by reductive amination may be used. In this method a polyamine with primary amines is reacted with a diketone or with an alkanedialdehyde to form an imine crosslinker which is then farther hydrogenated to the corresponding amine. This amine may be further reacted to form an antimicrobial effective quaternary ammonium group. In such a method, instead of dihaloalkanes or dialdehydes one may use a tri or polyhaloalkanes or polyaldehydes or polyketones.

According to yet another alternative, crosslinking may be affected by amidation with di or multi carboxylic acids. Yet alternatively, crosslinked polyamines can be prepared from the monomers where a crosslinking agent is added to the polymerization mixture. For example, crosslinked polyethylene imine (PEI) may be prepared by polymerization of aziridine in the presence of a low percentage of a bis aziridine that serves as crosslinking agent.

It should be noted that compositions of various polymeric chains may provide a range of properties that themselves may be an accumulation of the various polymer properties but more likely provide unexpected synergistic properties. Examples of such mixed polyamine nanoparticles include: crosslinking of aliphatic and aromatic polyamines such as polyethyleneimine and poly(4-vinyl pyridine) via a dihaloalkane; polyethylneimine and polyvinylamine; mixture of linear short chain and branched high molecular weight polyethyleneimines; interpenetrating compositions of polyamine within a polyamine scaffold such as polyethyleneimine embedded within crosslinked polyvinyl pyridine nanoparticles, or even a polyamine into a low density non-amine scaffold such as polystyrene nanoparticles. In other words, the use of polyamine combinations for the purpose of forming nanoparticles, either by chemical crosslinking or physical crosslinking (interpenetrating networks) may afford structures of varying properties (such as being able to better kill one bacteria vs. another type of bacteria). Such properties may be additive or synergistic in nature.

The preferred degree of cross-linking is from 1% to 20%, when crosslinking of from about 2% to about 5% is preferable. The crosslinking may prevent unfolding of the polymer and separation of the various polymeric chains that form the particle.

The preferred polymers useful for making particles according to the invention are those having chains made of 30 monomer units, preferably 100 monomer units that may be crosslinked using less than 10% of crosslinking agent. The longer the polymers are, the fewer crosslinking bonds are needed to afford an insoluble nanoparticle. Branched polymers are preferred for crosslinking as small amount of crosslinking is required to form insoluble nanoparticles.

An "aliphatic polymer" as used within the scope of the present invention refers to a polymer made of non-pyridinic monomers that may be substituted with various side groups, including (but not restricted to) aromatic side groups having a pyridine side group. Aliphatic polymers that may be included in particles according to the present invention may also comprise nitrogen atoms (as well as other heteroatoms) as part of the polymeric backbone. Non-limiting examples of aliphatic polymers are polyethylene imine (PEI), polyvinyl amine (PVA), poly(allyl amine) (PAA), poly(aminoethyl acrylate), aminomethyl styrene polymers, polypeptides with pending alkyl-amino groups, and chitosan.

The term "quaternary ammonium group" refers to a group of atoms consisting of a nitrogen atom with four alkyl groups attached thereto, wherein each of the alkyl groups is attached to the nitrogen through a carbon atom. Any number of the alkyl groups (0, 1, 2, 3, or 4) may be a portion(s) of the polymeric backbone. The term "long alkyl group" or chain refers to such an alkyl group or chain which is substituted on the nitrogen atom of the quaternary ammonium group and which has between 4 and 10 carbon atoms. Such term may also include an alkyl group or chain having between 4 and 10 carbon atoms and which folds back forming a cyclic structure, wherein the point of attachment or ring closure is the nitrogen atom of the quaternary ammonium group.

"Short alkyl groups" or chains have between 1 and 3 carbon atoms.

Preferably, the ammonium groups are chemically bound to the aliphatic polymer, namely they are bonded to said polymer via a covalent bond.

Polymeric particles of the present invention may also include quaternary ammonium groups that are not anti-microbially active, for instance, groups having no long alkyl group or more than one long alkyl group. However, the more anti-microbially active groups there are, the more preferred is the polymer, and a particle according to the invention is made of a polymer having at least one such group per polymeric chain.

As a quaternary ammonium group is positively charged, its charge should be balanced with an anion. Preferably, in a particle according to the invention this anion is a halide, e.g. fluoride, chloride, bromide or iodide, and fluoride is most preferred. Other possible anions include, but are not limited to, borohydride, bicarbonate, nitrate, phosphate, acetate, fumarate, succinate and sulfate.

In a preferred embodiment, the surface of the particle includes at least 1 anti-microbially active quaternary ammonium group per sq. nm.

The calculated density of active quaternary ammonium groups per 1 nm sq. of a particle made of such crosslinked PEI is about 16. If all imine groups are alkylated to be antimicrobially active, a density of about 16 quaternary ammonium groups per square nm is obtained. In the case of cross-linked PEI the requirement of at least one antimicrobially active quaternary ammonium group per 1 nm sq. requires at least about 5-10% alkylation of imines to antimicrobially active ammonium groups.

In a preferred embodiment, the polymeric particles according to the invention have functional groups that are capable of reacting with a host polymer or with monomers thereof. Such functional groups are designed to allow the particles to be bound chemically to a hosting matrix.

Nanoparticles Embedded in a Hosting Matrix

According to another aspect of the present invention, there is provided a polymeric matrix, comprising a polymeric host embedding polymeric particles according to the first aspect of the present invention.

Non-limiting examples of substances that may serve as hosts are ceramics, cements made of mixtures of polymeric material and inorganic solids, plant powders and particles compressed into a solid article, and organic and inorganic glues. Other substances may be selected from metal coatings and other solid, semisolid or gel-like materials.

In preferred embodiments, particles according to the invention are homogeneously distributed on the outer surface of the matrix in a surface concentration of between about 1 to about 100 particles per sq. ⁻µm. The distribution of the particles away from the outer surface, that is, their bulk concentration, may be similar to that on the outer surface. As a rule, the total surface of the particles preferably occupies at most about 20% of the surface of the matrix, preferably between 1% to 15%, more preferably between 1% to 5% and most about between 1% and 3% of the surface of the matrix.

Other rule that may help in constructing preferred matrix materials according to the invention is that on the average, every sq. ⁻µm of outer surface of matrix will have at least one portion with surface concentration of 1 anti-microbial active quaternary amine per sq. nm, and that the size of such portion will be at least 100 $nm^2$.

The polymeric particles may be physically entrapped within the matrix, chemically bound thereto, or both. In case the particles are to be chemically bound to the polymeric host, the particles have functional groups that are capable of reacting with the host polymer, or with monomers thereof.

According to a preferred embodiment, the polymeric matrix according to the invention has optical characteristics that are comparable to those of the polymeric host. This is obtained by using particles of small enough a size, and typically by using particles having size that is smaller than the wavelength of light, in which optical characteristics should be the same in the matrix and in the host. Particles of up to 300 nm in size are preferable for that purpose. Optical characteristics of the matrix and the host are said to be comparable if the two have the same refraction index (n) within tolerance of up to 10%, preferably up to 5%, and/or the same absorption coefficient ($^-\mu$) with tolerance of up to 10%, preferably up to 5%, all in a given range of wavelengths, preferably, visible light at a range of 400-700 nm.

In a preferred embodiment, a matrix according to the invention also comprises a strong reducing agent or a strong oxidizing agent (hereinafter, collectively, redox agent), such as boro-hydride, iodine, etc. The presence of the redox agent allows a short-term and extremely strong antiseptic effect while the long-lasting effect is achieved by the anti-microbially active quaternary ammonium groups of the polymeric particles.

A Method for Inhibition of Biological Species

According to another aspect of the invention there is provided a method for inhibition of "biological species", such as bacteria, parasites, fungi, yeast, protozoa and viruses, by contacting said biological species with a polymeric matrix according to the invention. The term "inhibition" is used to denote destruction, i.e. annihilation, of at least 95% of the species, preferably 99%, most preferably 99.99% of the species; reduction in the growth rate of said biological species; reduction in the size of the population of said biological species; prevention of growth of said species; causing irreparable damage to such species; destruction of a biofilm of said biological species; inducing damage, short term or long term, to a part or a whole existing biofilm; preventing formation of such biofilm; inducing biofilm management; or bringing about any other type of consequence which may effect such population or biofilm and impose thereto an immediate or long term damage (partial or complete).

The term "population" refers to a community of at least two members of a specific species or a combination thereof. It should be noted, however, that this definition does not intend to reflect on the ability of the particles of the invention to treat a single member of such population.

The term "biofilm" refers to a population of biological species attached to a solid surface. A biofilm population can include bacteria, fungi, yeasts, protozoa, and other microorganisms.

In a preferred embodiment, the inhibition is achieved by contacting the biological species with a matrix containing up to 5% w/w, more preferably up to 1% polymeric particles.

Accordingly, polymeric matrices according to the invention may find utility in a broad range of applications, where decontamination or growth prevention of biological species is required, as, for example in medicine artificial replacement of tissues such as bone, bone cements and joints (orthopedic), lenses (ophthalmology), blood vessels and stents, artificial heart valves (cardiology), artificial skin, implants (plastic surgery), intra uterin devices (gynecology), neurosurgical shunts, uretral stents coating for subcutaneous implants: insulin pumps, contraceptives, pacemakers. tubing and canulas used for intra venous infusion, tubing and canulas used for dialysis, surgical drainage tubing, urinary catheters, endotracheal tubes, wound covering materials, sutures, catheters of all kinds that are inserted temporarily in blood vessels as well as the urinary system, shunt for use in brain applications, surgical gloves, tips for ear examination, statoscope ends and other elements used by the medical personnel; in dentistry: dental adhesives, dental restorative materials such as all types of composite based materials for filling tooth-decay cavities, endodontic filling materials (cements and fillers) for filling the root canal space in root canal treatment, materials used for provisional and final tooth restorations or tooth replacement, including but not restricted to inlays, onlays, crowns, partial dentures (fixed or removable) dental implants, and permanent and temporary cements used in dentistry for various known purposes; plastic wear for medical and research laboratories; food packaging, mainly for dairy products and fresh meat; paints for ships, that prevent growth of biofilm, paints for bathrooms, and many others.

The antimicrobial property may protect the patient and the medical staff from cross contamination from patient to patient or from patient to the examiner. Self sterilizing packaging for medicines and items that enter the operation room are also beneficial. Applications out of the medical field may for example be in athlete shoes or the inner part of a shoe wherein bacteria tend to collect, tooth brushes and any brush that comes in contact with the human body, pet cages as well as other veterinary items, etc.

Preferred Polymers

According to another aspect of the invention there are provided aliphatic polymers that are suitable for making a particle according to the invention. It should be pointed out that other polymers, which per se are known in the art, may also be useful for making particles according to the invention. The polymer of the invention carries quaternary ammonium groups, which are substantively anti-microbially active.

Preferably, the quaternary ammonium groups of a polymer according to the invention is a nitrogen atom having only one bond to the polymer, in other words, the quaternary group is attached to the polymer backbone and not within the chain, and three bonds to non-polymeric groups, exactly one of which being at least a C4 aliphatic group and at most a C18 group, preferably at most a C10 group and most preferably a C8 group.

Preferably, the other non-polymeric group(s) attached to the nitrogen atom are $C_{1-3}$ aliphatic groups. The quaternary ammonium groups may be attached to the polymeric backbone directly (which allows one or two such groups per polymeric chain) or through a linker, which may be linked to each monomer or to some of the monomers.

The quaternary ammonium groups in polymers according to the invention have a positive charge, which is preferably balanced by a halide, most preferably by fluoride.

In a preferred embodiment, the polymer of the invention is cross-linked, such that it produces particles.

Possible cross-linking agent and methods, as well as possible counter ions were discussed above.

A Method of Making a Matrix

According to yet another aspect of the present invention there are provided methods for obtaining a polymeric matrix comprising a polymeric host embedding polymeric particles according to the invention, and particularly, methods for obtaining such matrices, wherein the particles' distribution in the host is substantially homogeneous. The term "substantially homogeneous distribution" is used to denote a distribution, characterized in that the standard deviation of the number of particles per sq. $^-\mu$m is no more than the average number of particles per sq. $-\frac{1}{4}$ m. A homogeneous distribution is required for reproducibility and product specifications.

If the distribution is not even, the product may exhibit different properties at different areas.

According to one method of the invention, the particles are added to the host together with a surface active compound, in an amount that does not adversely affect the anti-microbial effect of the particles, but allows homogeneous distribution of the particles in the host. Typical amount of a surface active compound that may be added to the particles is in the range of 0.1 to about 3% w/w of particles, preferably 1% w/w. This amount is dependent on the nature of the compound and the particles, the polymer composite and the process where these particles are incorporated in. For hydrophobic polymer compositions, a hydrophobic surface active compound such as Span, fatty acids, or fatty acid-PEG derivatives may be useful; and for hydrophilic polymer compositions, Poloxamer, PEG, or Tweens may be used to increase the compatibility of the nanoparticles in the polymer matrix.

According to another method in accordance with the invention, the polymer is first mixed with a compatibilizer, and than with the particles. Non-limiting examples to compatibilizers are monomers of the hosting polymer; monomers of the polymer, from which the particle is made; and oligmers of such monomers.

Another preferred method for obtaining polymeric host chemically bound to polymeric particles according to the invention is by polymerization of host's monomers in the presence of the polymeric particles.

A Method for Making Preferred Polymers

According to still another aspect of the present invention, there is provided a method for obtaining an aliphatic polymer, which carries quaternary ammonium groups, all of which being anti-bacterially active. The method comprising: selectively substituting one hydrogen atom on each primary amine with $C_{4-10}$ alkyl; and than substituting the other aminic hydrogen atoms (if exists) with $C_{1-3}$ alkyls.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1 is a schematic view of a particle according to one embodiment of the invention;

FIG. 2 is a schematic representation of a polymer that may be useful in making a particle according to some embodiments of the invention;

FIG. 3 is a schematic view of a matrix according to one embodiment of the invention;

FIG. 4 is an artist view of a particle according to one embodiment of the invention;

FIG. 5 is a schematic representation of a polymer according to one embodiment of the invention;

FIG. 11 depicts the Streptococcus mutans growth calibration curves included in all direct contact test experiments. Each growth curve is generated from five fold serial dilutions of the bacterial suspension allowing the calculation of bacterial inhibition.

FIG. 12 depicts full antibacterial activity after 6 months of aging of restorative samples loaded with 1% w/w of crosslinked PEI-quaternary ammonium into flowable composite resin. Letter codes of the PEI samples are in the footnote of Table 1.

DETAILED DESCRIPTION OF EXEMPLARY EMBODIMENTS

Figure 6:
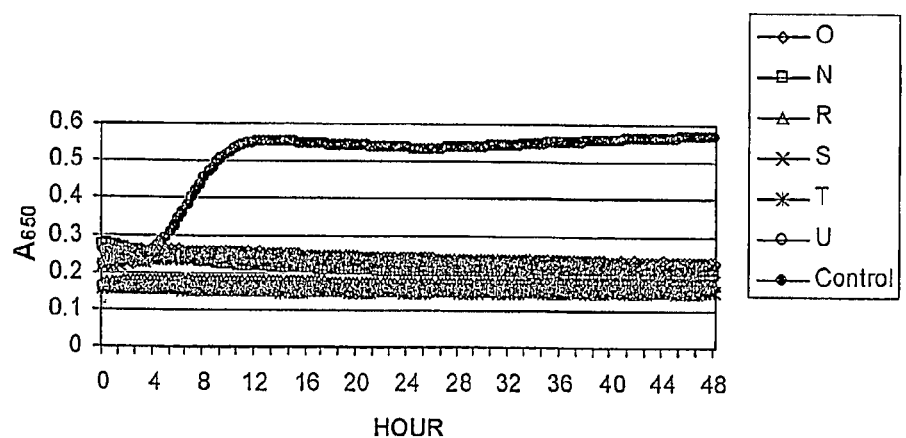
FIG. 6 depicts the antibacterial decay of the bacteria exhibited by composite resin samples incorporated with 1% w/w PEI nanoparticles and alkylated with various alkylation agents (relative to control—the commercial composite resin), where flowable composite was used as a negative control. Letter codes of the PEI samples are in the footnote of Table 1.

FIG. 1 shows schematically a particle 2 according to some preferred embodiments of the invention. The particle 2 has an inner portion 4 and an outer portion 6, wherein both inner and outer portions are made of the same aliphatic polymer. The inner portion 4 and the outer portion 6 of the particle 2 are made of substantially the same compound, such that the inner portion cannot dissociate from the outer portion, as the two portions are continuous and integral with each other. Thus, the dashed line 8, separating the inner portion 4 from the outer portion 6 is imaginary, and does not have any constructional importance or meaning.

FIG. 2 shows schematically a polymer 10 with antimicrobially active quaternary ammonium groups 12, 14, 16, and 18 each of which consisting of a nitrogen atom N chemically substituted onto or being a part of the polymer chain 10 and to three other alkyl groups. The nitrogen atom of the quaternary ammonium 12 has one bond to the polymeric chain 20, the nitrogen atom of the quaternary ammonium 14 has two bonds to the polymeric chain, the nitrogen of the ammonium 16 is connected to a side chain 22 of the polymer 10, rather than to the polymeric backbone 20, and the nitrogen of the ammonium 18 is bound to three polymeric chains 20, 20' and 20", all forming part of the polymer 10. Each nitrogen atom N has exactly one alkyl group R which is a long alkyl group. The other groups, W are short alkyl groups.

FIG. 3 shows a schematic view of a polymeric matrix 30, comprising a polymeric host 32 embedding polymeric particles 34. FIG. 4 shows a single such particle in the artist eye. The particle 34 has many long alkyl chains 36 protruding therefrom. The alkyl chains 36 are groups that substitute nitrogen atoms in antimicrobially active quaternary ammonium groups of the polymer that forms the particle 34. It should be noted, however, that in reality, there are at least one such long alkyl chain per sq. nm of particle, so if the particle 34 is 100 nm in diameter, it is covered with at least about 36,000 protruding long alkyl chains, and not so few as illustrated in the figure.

As shown in FIG. 3, the particles 34 are homogeneously distributed on the outer surface(s) 38 of the matrix 30. In the example shown in the figure, the total surface covered with long alkyl chains that protrude out of the matrix material 32 is about 1% of the outer surface 38 of the matrix 30.

FIG. 5 schematically shows a polymer 50 according to the present invention. The polymer 50 has quaternary ammonium groups 52 and 54, each consisting of a nitrogen atom N having only one bond to the polymeric backbone 56, and three bonds to non-polymeric groups, exactly one of which (R) being a long alkyl group. The other groups (W) are methyl groups.

The quaternary ammonium groups 52 are attached to the polymeric backbone 56 directly (which allows one or two such groups per polymeric chain). The quaternary ammonium groups 54 are attached to the polymeric backbone through a linker 56.

A polymer such as the polymer 50 may be obtained from a polymer that contains primary amines by alkylation thereof with long alkyl groups under conditions that allow alkylation of only primary amines, and than methylation of the resulting secondary amines, under conditions that convert them into quaternary amines.

EXAMPLES

Example 1

Effect of the Alkyl Chain on the Antimicrobial Activity of the Compound

Antibacterial activity of PEI is dependent on the quality and quantity of quaternary amines. Therefore it was decided in the course of the investigation leading to the present invention to increase both by alkylation with alkyl halides of various lengths followed by methylation in order to increase degree of amino group substitution. Alkylation agents impart hydrophobic nature to the hydrophilic PEI. This N-alkylation should make the polymer more hydrophobic and methylation also raises its positive charge by converting PEI's primary, secondary and tertiary amino groups into cationic quaternary amino groups. Studies on PEI nanostructured samples, modified with various alkylation agents based on alkyl bromides, were made to evaluate their antibacterial properties as a function of length alkyl group. PEI nanostructured materials were prepared via crosslinking with dibromopentane followed by alkylation with alkyl bromides and methylation with methyl iodide. Alkane dihalides of 2 to 8 methylene groups are preferred. 1,5-dibromopentane was chosen as appropriate crosslinking agent, 1,4-Dibromobutane and 1,6-dibromohexane may be used also as suitable crosslinking agents.

A. Crosslinking of Polyethyleneimine (PEI) with Dibromopentane

Aqueous solution of PEI was lyophilized to dryness before use. PEI (18.65 g, 0.434 mol) of the 1.000.000-600.000 Da was dissolved in 186 ml of absolute ethanol. Dibromopentane (17.35 mmol, 2.4 ml) was added at a 1:0.04 mole ratio (PEI monomer/dibromopantane). The crosslinking reaction was carried out at reflux conditions for 24 hours. Then excess of sodium hydroxide (1 g) dissolved in methanol was added to collect released HBr. Reaction was continued at the same conditions for additional 24 hours. After cooling to room temperature, the resulting residue was purified from NaBr by gravitational filtration. Filtrate was evaporated to dryness under reduced pressure to yield yellow viscous residue which upon mixing in ethanol forms a very fine powder. The degree of crosslinking with dibromopentane was determined by microanalysis and found to be 100%. Microanalysis: % C=48.05, % N=21.20. $^1$H-NMR (CDCl$_3$): 1.43 ppm (m, 2H, alkyl hydrogens), 1.58 ppm (m, 4H, alkyl hydrogens), 2.1-3 ppm (m, 4H of PEI hydrogens and 4H of alkyl hydrogens). ALV (radius, nm): 27 nm (97%).

B. Alkylation of Crosslinked PEI-Based Nanoparticles with Bromooctane

Crosslinked PEI (1.9 g, 45 mmol) was dispersed in 20 ml of absolute ethanol. 7.73 ml of bromooctane (45 mmol, 1 equimolar) was added to suspension containing 1 equimolar amount of the crosslinked PEI nanoparticles. Alkylation reaction was carried out at reflux conditions for 24 hours. Then excess of sodium hydroxide (2 g.), dissolved in methanol, was added to collect released HBr. Reaction was continued at the same conditions for additional 24 hours. After cooling to room temperature, the resulting residue was purified from NaBr by gravitational filtration. Filtrate was evaporated to dryness under reduced pressure to yield yellow viscous liquid. Resulted crude was washed with acetone and DDW to remove traces of bromooctane and NaOH, respectively.

The same procedure was repeated with various alkylbromides including bromobutane, bromohexane, bromooctane, bromodecane and bromohexadecane.

Compounds based on alkylation with longer alkylbromides such as bromodecane and bromohexadecane were purified by precipitation in methanol. The degree of alkylation with bromoalkanes was determined by microanalysis and found to be 80%. $^1$H-NMR (CDCl$_3$): 0.86 ppm (t, 3H, CH$_3$, octane hydrogens), 1.24 ppm (m, 10H, —CH$_2$—, octane hydrogens), 1.39 ppm (m, 2H, —CH$_2$—, octane hydrogens), 2.36-2.7 ppm (m, 4H, —CH$_2$—, PEI hydrogens and 2H of octane hydrogens).

C. Quaternization of Alkylated PEI-Based Nanoparticles 730 mg of the previously obtained octane-alkylated PEI (4.7 mmol) was dispersed in 10 ml of absolute ethanol. Excess of methyl iodide (24 mmol) was added. Reaction was carried out at 60° C. for 48 hours. An equimolar amount of sodium bicarbonate (0.4 g) was added to collect released HI during methylation step. Neutralization was continued at the same conditions for additional 24 hours. NaI salt was discarded by filtration and filtrate was evaporated under reduced pressure. Traces of unreacted methyl iodide were removed by evaporation. Resulted yellow crude was vacuum-dried over NaOH over night to yield 660 mg of the product. The same procedure was repeated with all, previously mentioned, alkylated PEI nanoparticles. The degree of the methylation was determined by microanalysis (% I) and found to be 90%. FT-IR (KBr): 3400 cm$^{-1}$ (N—H), 2950 cm$^{-1}$ and 2850 cm$^{-1}$ (C—H), 1617 cm$^{-1}$ (N—H$_2$), 1460 cm$^{-1}$ (C—H), 967 cm$^{-1}$ quaternary nitrogen. $^1$H-NMR (DMSO): 0.845 ppm (t, 3H, CH$_3$, octane hydrogens), 1.24 ppm (m, 10H, —CH$_2$—, octane hydrogens), 1.65 ppm (m, 2H, CH, octane hydrogens), 3.2-3.6 ppm (m, CH$_3$ of quaternary amine, 4H of PEI and 2H of the octane chain).

D. Cross Linked Quaternary PEI Nanoparticles in Dental Composites

The experimental specimens were prepared by adding the quaternizied PEI-based nanoparticles into commercially available dental composite (Filtek Flow 47% Zirconia/silica average particle size 0.01-6.0μ; BIS-GMA, TEGDMA; 3M Dental St Paul, Minn.). The addition was carried out on a base of 1% w/w relative to the flowable composite. Antibacterial effect of the quaternizied PEI nanostrutured materials, modified with various alkylation agents, was examined against *Streptoccocus mutans* (ATCC#27351) in direct contact with bacteria. Strong antibacterial decay of the bacteria was exhibited by all composite resin samples incorporated with 1% w/w PEI nanoparticles, alkylated with various alkylation agents including bromobutane, bromohexane, bromooctane and bromodecane, relative to the commercial composite resin as shown in the FIG. 6, where flowable composite was used as a negative control.

Figure 7A:
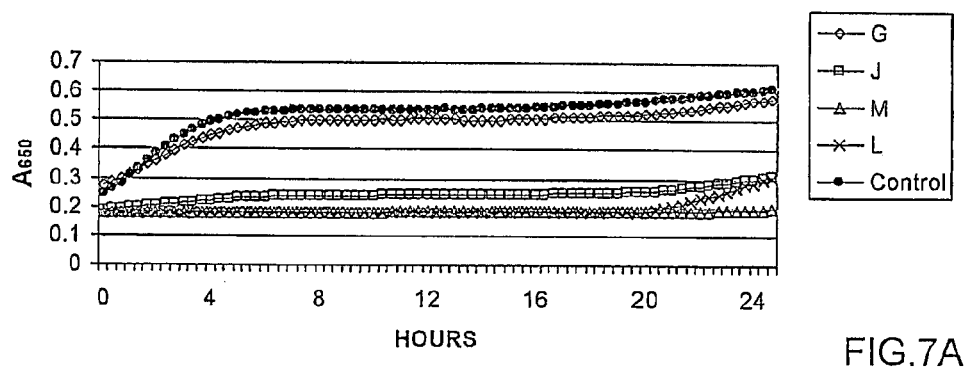
FIGS. 7A and 7B depict the antibacterial stability of the PEI nanostructured samples modified with long chain alkyls over one week (FIG. 7A) and one month (FIG. 7B) against Streptoccocus mutans (commercial flowable composite was used as control).
Figure 7B:
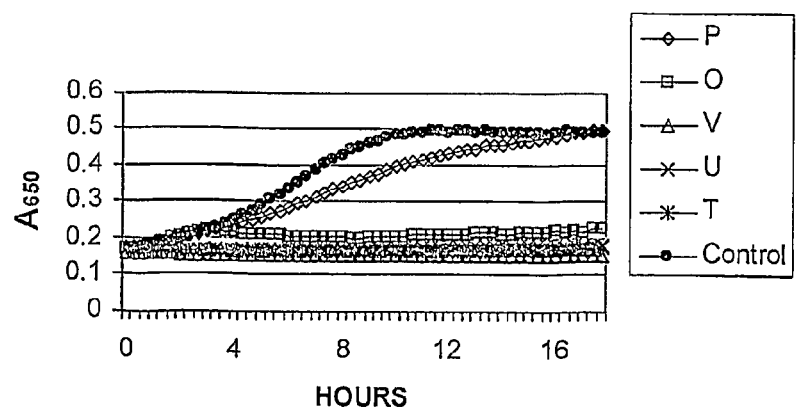
Figure 8A:
FIG. 8 is a scanning electron microscopy pictures of (A) bacteria surface before treatment and (B) bacteria surface after treatment with flowable composite and 1% PEI nanoparticles.
Figure 8B:
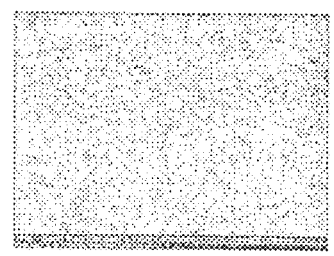

The antibacterial stability of the compounds was examined for several weeks. The PEI nanostructured samples modified with long chain alkyls, including hexane, octane and decane chains, demonstrated stable antibacterial activity against *Streptoccocus mutans* for more than four weeks as shown in FIGS. 7A-B, where flowable composite was used as negative control.

The strong antimicrobial properties of the tested compounds are attributed to the hydrophobic nature of the PEI nanoparticles due to modification with long chain alkylation agents.

Example 2

Effect of the Crosslinking on the Nanoparticle Stability Evaluated by Antibacterial Activity To examine crosslinking contribution to the nanoparticle stability, crosslinked and non-crosslinked PEI nanoparticles were prepared. Non-crosslinked PEI nanostructured compounds were prepared as crosslinked PEI nanoparticles, including alkylation step with bromooctane followed by quaternization with methyl iodide, avoiding crosslinking step with dibromopentane. The purpose of this step was to evaluate nanoparticle formation and stability as a function of the crosslinking, estimate their bactericidal potency in the immediate contact with bacteria and during prolong period.

A. Alkylation of PEI with Bromooctane

Alkylation of PEI with bromooctane was followed as previously described in Example 1.

The degree of alkylation with bromooctane was determined by microanalysis and found to be 71%. $^1$H-NMR (CDCl$_3$): 0.86 ppm (t, 3H, CH$_3$ octane hydrogens), 1.24 ppm (m, 10H, —CH$_2$—, octane hydrogens), 1.39 ppm (m, 2H, —CH$_2$—, octane hydrogens), 2.36-2.7 ppm (m, 4H, —CH$_2$—, PEI hydrogens and 2H of octane hydrogens).

B. Quarternarization of Alkylated PEI

Quaternization of alkylated PEI was followed as previously described in Example 1.

The degree of the methylation was determined by microanalysis (% I) and found to be 90%. FT-IR: 3400 cm-1 (N—H), 2950 cm-1 and 2850 cm-1 (C—H), 1617 cm-1 (N—H2), 1460 cm-1 (C—H), 967 cm-1 quaternary nitrogen. $^1$H-NMR (DMSO): 0.845 ppm (t, 3H, CH$_3$ octane hydrogens), 1.24 ppm (m, 10H, —CH$_2$—, octane hydrogens), 1.65 ppm (m, 2H, CH, octane hydrogens), 3.2-3.6 ppm (m, CH$_3$ of quaternary amine, 4H of PEI and 2H of the octane chain).

In contrast to the crosslinked PEI-based nanoparticles (see octane-alkylated PEI-based samples in Example 1), non-crosslinked quaternized PEI compounds are not able to form stable nanoparticles in each solvent. However, they formed nanostructured shapes in aqueous solvents due to their hydrophobic nature. Crosslinking effect was examined by antibacterial evaluation against *Streptoccocus mutans* bacteria.

Example 3

Effect of the Crosslinking Degree on the Nanoparticle Size

The purpose of this step was to prepare PEI-based nanoparticles at various degrees of crosslinking, evaluate their size as a function of the degree of the crosslinking and examine their antibacterial potency.

A. Crosslinking of Polyethyleneimine (PEI) with Dibromopentane

Aqueous solution of PEI was lyophilized to dryness before use. Three samples of the PEI (18.65 g, 0.434 mol) of the 1.000.000-600.000 Da were dissolved in 186 ml of absolute ethanol. Dibromopentane was added at either 1:0.01, 1:0.05, 1:0.2 mole ratio (PEI monomer/dibromopantane). Crosslinking reaction was carried out at reflux conditions for 24 hours. Then excess of sodium hydroxide (1 g) dissolved in methanol was added to collect released HBr. Reaction was continued at the same conditions for additional 24 hours. After cooling to room temperature, the resulting residue was purified from NaBr by gravitational filtration. Filtrate was evaporated to dryness under reduced pressure to yield yellow viscous liquid. The degree of crosslinking with dibromopentane was determined by microanalysis and found to be 99%. 1H-NMR (CDCl3): 1.43 ppm (m, 2H, alkyl hydrogens), 1.58 ppm (m, 4H, alkyl hydrogens), 2.1-3 ppm (m, 4H of PEI hydrogens and 4H of alkyl hydrogens).

B. Alkylation of PEI-Based Nanoparticles with Bromooctane

Alkylation of PEI with bromooctane was followed as previously described in Example 1.

The degree of alkylation with bromooctane was determined by microanalysis and found to be 75%. $^1$H-NMR (CDCl$_3$): 0.86 ppm (t, 3H, CH$_3$ alkyl hydrogens), 1.24 ppm (m, 10H, —CH$_2$—, alkyl hydrogens), 1.39 ppm (m, 2H, —CH$_2$—, alkyl hydrogens), 2.36-2.7 ppm (m, 4H, —CH$_2$—, PEI hydrogens and 2H of alkyl hydrogens).

C. Quaternization of the Alkylated PEI-Based Nanoparticles

Quaternization of alkylated PEI was followed as previously described in Example 1.

The degree of the methylation was determined by microanalysis (% I) and found to be 90%. FT-IR: 3400 cm$^{-1}$ (N—H), 2950 cm$^{-1}$ and 2850 cm$^{-1}$ (C—H), 1617 cm$^{-1}$ (N—H$_2$), 1460 cm$^{-1}$ (C—H), 967 cm-1 quaternary nitrogen. $^1$H-NMR (DMSO): 0.845 ppm (t, 3H, CH3, octane hydrogens), 1.24 ppm (m, 10H, —CH$_2$—, octane hydrogens), 1.65 ppm (m, 2H, CH, octane hydrogens), 3.2-3.6 ppm (m, CH$_3$ of quaternary amine, 4H of PEI and 4H of the octane chain).

Example 4

PEI Concentration Effect on the Nanoparticle Size

The purpose of this step was to prepare crosslinked nanoparticles at different PEI concentrations, evaluate their obtained size as a function of the concentration and examine their antibacterial potency.

A. Crosslinking of Polyethyleneimine (PEI) with Dibromopentane

Aqueous solution of PEI was lyophilized to dryness before use. Three samples of the PEI (18.65 g, 0.434 mol) of the 1.000.000-600.000 Da were dissolved in 93 ml, 186 ml and 372 ml, respectively, of absolute ethanol. Dibromopentane (17.35 mmol, 2.4 ml) was added at 1:0.04 mole ratio (PEI monomer/dibromopantane). Crosslinking reaction was carried out at reflux conditions for 24 hours. Then excess of sodium hydroxide (1 g) dissolved in methanol was added to collect released HBr. Reaction was continued at the same conditions for additional 24 hours. After cooling to room temperature, the resulting residue was purified from NaBr by gravitational filtration. Filtrate was evaporated to dryness under reduced pressure to yield yellow viscous liquid. The degree of crosslinking with dibromopentane was determined by microanalysis and found to be 100%. $^1$H-NMR (CDCl$_3$):

1.43 ppm (m, 2H, alkyl hydrogens), 1.58 ppm (m, 4H, alkyl hydrogens), 2.1-3 ppm (m, 4H of PEI hydrogens and 4H of alkyl hydrogens).

B. Alkylation of Crosslinked PEI with Bromooctane

Alkylation of PEI with bromooctane was followed as previously described in Example 1.

The degree of alkylation with bromoalkanes was determined by microanalysis and found to be 78%. $^1$H-NMR (CDCl$_3$): 0.86 ppm (t, 3H, CH$_3$, alkyl hydrogens), 1.24 ppm (m, 10H, —CH$_2$—, alkyl hydrogens), 1.39 ppm (m, 2H, —CH$_2$—, alkyl hydrogens), 2.36-2.7 ppm (m, 4H, —CH$_2$—, PEI hydrogens and 2H of alkyl hydrogens).

C. Quaternization of Alkylated PEI-Based Nanoparticles

Quaternization of alkylated PEI was followed as previously described in Example 1.

The degree of the methylation was determined by microanalysis (% I) and found to be 85%. FT-IR: 3400 cm-1 (N—H), 2950 cm-1 and 2850 cm-1 (C—H), 1617 cm-1 (N—H2), 1460 cm-1 (C—H), 967 cm-1 quaternary nitrogen. 1H-NMR (DMSO): 0.845 ppm (t, 3H, CH3, alkyl hydrogens), 1.24 ppm (m, 10H, —CH$_2$—, alkyl hydrogens), 1.65 ppm (m, 2H, CH, alkyl hydrogens), 3.2-3.6 ppm (m, CH$_3$ of quaternary amine, 4H of PEI and 2H of the alkyl chain).

According to the ALV (radius, nm) analysis, negligible effect was detected on the size of the crosslinked PEI nanoparticles as function of the PEI concentration during crosslinking step. High and low concentrated solution caused a small difference of the resulted nanoparticle size: 46 nm and 32 nm, respectively. Further alkylation with bromooctane followed by quaternization with methyl iodide resulted in similar size of the nanoparticles. Their bactericidal potency was also examined. Both of them demonstrated high antibacterial action when were incorporated at 1% w/w with restorative material. Alkylation agent can also play a significant role in the final nanoparticle size, however in this step only bromooctane was used as alkylation agent.

Example 5

Molecular Weight Effect of the Starting Material

Bactericidal potencies of the alkylated PEI are well known and are proven very effective against a variety of Gram-positive and Gram-negative bacteria. An antibacterial mode of action can be also attributed to the various molecular weights of the alkylated PEI. PEI chains indeed must be polymeric to exert their bactericidal effect. In this experiment 1000-, 25-kDa and 600 Da PEI starting materials were synthesuzed and their antibacterial potency was evaluated as function of the PEI molecular weight.

A. Crosslinking of Polyethyleneimine (PEI) with Dibromopentane

Crosslinking of polyethyleneimine with dibromopentane was followed as previously described in Example 1.

The degree of crosslinking with dibromopentane was determined by microanalysis and found to be 96%. $^1$H-NMR (CDCl$_3$): 1.43 ppm (m, 2H, alkyl hydrogens), 1.58 ppm (m, 4H, alkyl hydrogens), 2.1-3 ppm (m, 4H of PEI hydrogens and 4H of alkyl hydrogens).

B. Alkylation of Crosslinked PEI with Bromooctane and Methylation with Methyl Iodide Alkylation and methylation reactions were carried out as mentioned in Example 1. Degree of methylation of the alkylated PEI nanoparticles was determined by microanalysis and found to be 90%.

Prepared quaternized PEI-based nanoparticles were characterized by $^1$H-NMR analysis, microanalysis, ALV (size definition) and zeta measurement. For evaluation of the PEI-based nanoparticle antibacterial activity, dental material was incorporated with tested nanoparticles at 1% w/w. The tests were presented with immediate contact effect and prolong bactericidal activity which was examined for several weeks. As expected, high molecular weight based PEI nanoparticles possess bactericidal activity during long period, while low molecular weight samples, show moderate or no antibacterial effect at all. These results demonstrate that PEI must be polymeric to be bactericidal.

Example 6

Vinyl Group Substitution of Alkylated PEI Nanoparticles

Alkylated PEI nanoparticles were substituted with acryloyl chloride followed by a methylation step to further polymerization with dental composite. Polymerization of the PEI based nanoparticles with restorative material may minimize migration of the nanoparticles to the surrounding environment and prolong its antibacterial effect.

A. Crosslinking of Polyethyleneimine (PEI) with Dibromopentane

Aqueous solution of PEI was lyophilized to dryness before use. PEI (18.65 g, 0.434 mol) of the 1.000.000-600.000 Da was dissolved in 186 ml of absolute ethanol. Dibromopentane (1.2 ml, 8.675 mmol) was added at 1:0.02 mole ratio (PEI monomer/dibromopantane). Crosslinking reaction was carried out at reflux conditions for 24 hours. Then excess of sodium hydroxide (1 g) dissolved in methanol was added to collect released HBr. Reaction was continued at the same conditions for additional 24 hours. After cooling to room temperature, the resulting residue was purified from NaBr by gravitational filtration. Filtrate was evaporated to dryness under reduced pressure to yield yellow viscous liquid.

B. Alkylation of Crosslinked PEI with Bromohexane

Crosslinked PEI-based nanoparticles (1.9 g, 45 mmol) were dispersed in 20 ml of absolute ethanol. 7.73 ml of bromohexane (45 mmol, 1 equimolar) was added to suspension containing 1 equimolar amount of the crosslinked PEI nanoparticles. Alkylation reaction was carried out at reflux conditions for 24 hours. Then excess of sodium hydroxide (2 g.), dissolved in methanol, was added to collect released HBr. Reaction was continued at the same conditions for additional 24 hours. After cooling to room temperature, the resulting residue was purified from NaBr by gravitational filtration. Filtrate was evaporated to dryness under reduced pressure to yield yellow viscous liquid. Traces of unreacted bromohexane were removed by reduced pressure with oil pump. The degree of alkylation with bromohexane was determined by microanalysis and found to be 72%. Microanalysis: % C=67.94,% N=13.81. FT-IR: 3300 cm-1 (N—H); 2950 cm-1, 2930 cm-1 and 2850 cm-1 (C—H); 1460 cm-1 (C—H). 1H-NMR (CDCl3): 0.88 ppm (t, 3H, CH3, alkyl hydrogens), 1.27 ppm (m, 6H, —CH2-alkyl hydrogens), 1.4 ppm (m, 2H, —CH$_2$—, alkyl hydrogens), 3.2-3.4 ppm (m, 4H, —CH$_2$—, PEI hydrogens and 2H of alkyl hydrogens).

C. Conjugation of Acryloyl Chloride to the Alkylated PEI-Based Nanoparticles

Hexane alkylated PEI-based nanoparticles (1.37 g, 6.59 mmol) were dispersed in 50 ml of anhydrous THF and 0.69 g of the anhydrous 2% crosslinked 4-vinylpyridine (6.6 mmol) was added as proton sponge to collect released HCl during conjugation. 1 equimolar of acryloyl chloride (0.5 ml, 6.59 mmol) was added. Reaction was carried out at 40 C, dark, vigorous mixing and nitrogen atmosphere for 24 h. 4-vinylpyridinium salt was discarded by filtration and filtrate was evaporated to dryness under reduced pressure. Traces of the unreacted acryloyl chloride were removed by evaporation to yield 1.16 g of the yellow solid that was vacuum-dried over NaOH over night. Degree of the substitution with acryloyl chloride was determined by 1H-NMR and found to be 4.5%. 1H-NMR (DMSO): 0.9 ppm (m, 3H, hexane hydrogens), 1.3 ppm (m, hexane hydrogens, 6H), 1.7 ppm (m, aliphatic hydrogens of hexane, 2H), 3.1-3.4 ppm (m, a 4H hydrogens of PEI and 2H of the hexane chain), 5.9 ppm (d, olefin hydrogen, 1H), 6.1 ppm (d, olefin hydrogen, 1H) and 6.3 ppm (d, olefin hydrogen, 1H). FT-IR: 3400 cm-1 (N—H); 2950 cm-1, 2930 cm-1 and 2850 cm-1 (C—H); 1650 cm-1 (amide vibration) and 1460 cm-1 (C—H).

D. Quaternization of Alkylated PEI 105 mg of the alkylated PEI (0.5 mmol) was suspended in 50 ml of anhydrous THF and 0.26 ml of the anhydrous diisopropylethylamine (1.53 mmol) was added to collect released HI during methylation. Excess of methyl iodide (0.1 ml, 1.53 mmol) was added. Reaction was carried out at 40 C, dark, vigorous mixing and nitrogen atmosphere for 40 h. Ammonium salt was discarded by filtration and filtrate was evaporated to dryness under reduced pressure. Traces of unreacted methyl iodide were removed by evaporation. The resulted yellow crude was vacuum-dried over NaOH over night to yield 100 mg of the product. The degree of the methylation was determined by microanalysis and found to be 90%. Microanalysis: % C=46.8; % N=7.21. 1H-NMR (DMSO): 0.83 ppm (m, 3H, hexane hydrogens), 1.18 ppm (m, hexane hydrogens, 6H), 1.27 ppm (m, aliphatic hydrogens of hexane, 2H), 3.1-3.4 ppm (m, 4H hydrogens of PEI, 3H of the methyl of the quaternary amine and 2H of the hexane chain), 5.9 ppm (d, olefin hydrogen, 1H), 6.0 ppm (d, olefin hydrogen, 1H) and 6.1 ppm (d, olefin hydrogen, 1H).

According to the $^1$H-NMR analysis, alkylated PEI nanoparticles were substituted with 4.5% mol/mol of the acryloyl chloride relative to the amount of the PEI monomers. Quaternization of the compound was completed with methyl iodide. Obtained compound was polymerized with dental composite before test by UV irradiation and its antibacterial effect was examined against *Streptoccocus mutans* in direct contact with bacteria. Data analysis was evaluated by the absorbance measurements. The loss of the antibacterial properties of the tested compound may be prevented by the polymerization of the antibacterial agent with restoration materials and its effectiveness can be kept during prolong period.

Example 7

Comparison with Pyridinium-Type Based Nanoparticles and Counter Ion Effect

Pyridinium-type based nanoparticles were next tested as appropriate candidates for effective bacterial decay.

A. Suspension Polymerization of the 4-Vinylpyridine (4-VP)

The polymerization reaction of 4VP and divinylbenzene (DVB) (1% mol/mol to 4VP) was carried out in a three-necked round bottom flask equipped with a nitrogen inlet and reflux condenser. 1.08 ml (9.9 mmol) of 4VP and DVB (0.01 equimolar, 0.099 mmol) were dissolved in 0.5 ml of N-methylpyrrolydon. Polymerization was carried out in 100 ml of DDW using 10 mg of AIBN as an initiator and polyvinyl alcohol (0.8%) as a dispersing agent at 80° C. in dark under a nitrogen atmosphere. White suspension was obtained within 7 hours. The polymerized crosslinked particles were collected by filtration followed by washing with ethanol to remove N-methylpyrrolydon and DDW to remove polyvinyl alcohol. The product was vacuum-dried over NaOH over night. FT-IR (KBr): 1418 cm$^{-1}$ (symmetric C—N stretching vibration) and 825 cm$^{-1}$ (C—H out of plane bending vibration).

B. Quaternization of the Pyridine Rings

Quaternization of tertiary amine groups of the pyridine rings was carried out with excess of bromooctane. 0.2 gr (1.9 mmol) of the polymerized 4VP was dispersed in 30 ml of absolute ethanol and 2.85 mmol (1.5 equimolar) of the bromooctane was added. Reaction was carried out at reflux conditions with vigorous mixing for 48 hours. The product was collected by filtration followed by washing with ethanol to remove unreacted bromooctane and DDW. The brown crude was vacuum-dried over night over NaOH. The degree of quaternarization with bromooctane was determined by microanalysis (% Br) and found to be 84%. FT-IR (KBr): 1418 cm$^{-1}$ (symmetric C—N stretching vibration) and 1637 cm$^{-1}$ (quaternized pyridine rings).

C. Fluorination of the Pyridinium Polymers 0.2 g (1.7 mmol) of the quaternized p-4VP was dispersed in absolute ethanol and excess of NaF (50 equimolar, 0.084 mol) was added. Conversation into fluoride form was carried out at reflux conditions for 72 hous. The procedure was repeated with additional portion of NaF (50 equimolar) and reaction was continued at the same conditions for additional 24 hours. The resulted product was collected by filtration, washed with ethanol and DDW to remove unreacted NaF and NaBr. The obtained dark-green crude was vacuum-dried over NaOH over night. The degree of fluorination was determined by microanalysis (% F) and was found to be 81%. Microanalysis: % F=6.39, traces of bromide were detected.

Suspension polymerization of 4VP with different degree of crosslinking with DVB, starting from 1 up to 30% mol/mol relative to 4-VP, followed by quaternization with bromooctane and bromohexane resulted in nanoparticles ranging from 400 nm to 1 micron in diameter. Obtained pyridinium-type nanoparticles were characterized by volhard titration, microanalysis, coulter counter (size measurement) and zeta analysis. All prepared nanoparticles exhibit constant positive charge about 45 mV. Unfortunately, these nanoparticles were found completely inactive when were incorporated in the restorative material even up to 5% load while were found to be antibacterial effective as free nanoparticles. Conversation bromide form pyridinium-type nanoparticles into fluoride form resulted in an exchange of its properties. Fluoride salt based nanoparticles incorporation in dental restoration compositions resulted in a high bacterial decay.

Example 8

Incorporation of the 1% Prepared PEI Nanoparticles into Restoration Composites is Effective Against Bacteria on Contact The purpose of this step was to examine the antibacterial activity of previously described PEI nanoparticles incorporated into a dental composition at 1% w/w.

A. Preparation of the Bacteria

*Streptococcus mutans* (ATCC#27351) a strain originally isolated from dental plaque was used in the present study. Bacteria were cultured overnight in 5 ml of brain-heart infusion broth (BHI) (Difco, Detroit, Mich., USA), at 37° C. To avoid large bacterial aggregates or long streptococcal chains, the top 4 ml of the undisturbed bacterial culture were transferred to a new test tube and centrifuged for 10 min at 3175×g. Supernatant was discarded and bacteria were resuspended in 5 ml phosphate buffered saline (PBS) (Sigma, St. Louis, Mo., USA) and vortexed gently for 10 sec. Each bacterial suspension was adjusted to an optical density 1 at 650 nm. Ten microliters from ten fold serial dilutions were plated on BHI agar to determine colony-forming units per milliliter. BHI and PBS were supplemented with bacitracin 0.0625 gr/ml (Sigma, St. Louis, Mo., USA), to minimize external contamination.

B. Composition of Materials Used

The experimental specimens were prepared by adding the synthesized polymer Filtek Flow (47% Zirconia/silica average particle size 0.01-6.0μ; BIS-GMA, TEGDMA; 3M Dental St Paul, Minn.) a commercial restorative composite resin. The addition was carried out on a base of 1% w/w. After the polymer was added to the composite resin it was uniformly mixed with a spatula.

C. Preparation of the Microtiter Plate

Twenty two samples of various synthesized PEI polymers incorporated into a commercial composite resin at a 1% w/w were tested.

A microtiter plate (96-wells flat bottom Nunclon, Nonc, Copenhagen, Denmark) was vertically positioned. Using a flat-ended dental instrument (dental spatula) the sidewalls of 7 wells were coated evenly with an equal amount of the same tested specimen. Special care was taken to leave the bottom of the well untouched in order to avoid false readings during the incubation in the spectrophotometer. The materials were polymerized according to the manufacturers' instructions. Seven wells in the same microtiter plate coated with the commercial composite resin only with no synthesized polymer served as a positive control.

D. Direct Contact Between Bacteria and the Tested Materials

A 10 μl of bacterial suspension (ca. $10^6$ bacteria) was placed on each tested material sample in a set of 7 wells, and the plate was incubated at a vertical position for 1 hr at 37° C. During this incubation period, the suspension's liquid evaporated and a thin layer of bacteria was achieved ensuring direct contact between all bacteria and the tested surface as demonstrated by scanning electron microscopy (data not shown).

The plate was then placed horizontally and 220 μl of brain-heart infusion broth were added to each well containing the material.

E. Kinetic Measurements of Bacterial Growth

The microtitre plate was placed in a temperature controlled microplate spectrophotometer (VERSAmax, Molecular Devices Corporation, Menlo Oaks Corporate Centre, Menlo Park, Calif., USA), which was set to 37° C. with 5 sec vortex prior to every reading. Bacterial outgrowth was estimated by the following OD changes in each well at 650 nm every 20 minutes for 12-24 hours.

F. Data Analysis

The absorbance measurements were plotted resulting in bacterial growth curves for each well in the microtiter plate. The linear portion of the logarithmic growth phase was subjected to statistical analysis. Results are expressed in two parameters; the slop (a) and the constant (b) of a linear function ax+b=y derived from the ascending segment of the bacterial growth curve. The slop (a) and the constant (b) correlate with the growth rate and the initial number, respectively. The data was analyzed by one way ANOVA, and Tukey multiple comparison test. Level of statistical significance was determined at $p<0.05$.

G. Agar Diffusion Test

S. mutans previously prepared 200 μl of bacterial suspension was spread on Mitis salivarius agar (MSB) (Difco, Detroit, Mich., USA) supplemented with bacitracin 0.0625 gr/ml (Sigma, St. Louis, Mo., USA) and three light polymerized specimens of each tested material were placed on the surface. The plates were incubated for 48 h at 37° C. After the incubation the inhibition zone around each specimen was observed.

H. Results

These cationic polymeric nanoparticles with quaternary ammonium groups have been incorporated into a dental restorative composite at low concentrations (1%). The majority of the tested compounds were very effective by immediate contact (FIGS. 6, 7A and 7B) summarized in Table 1.

TABLE 1

Antibacterial activity of various compounds incorporated into dental composite materials.

| Dental material | Antibacterial Compound | Content (wt %) | ADT[a] growth inhibition | | DCT[b] percent inhibition | |
|---|---|---|---|---|---|---|
| | | | A | A[1] | B | B[1] |
| Flowable | A | 1 | − | − | 100 | 0 |
| | B | 1 | − | − | 100 | 0 |
| | C | 1 | − | − | 100 | 0 |
| | D | 1 | − | − | 100 | 100 |
| | E | 1 | − | − | 100 | 0 |
| | F | 1 | − | − | 100 | 0 |
| | G | 1 | − | − | 100 | 25 |
| | H | 1 | − | − | 100 | 0 |
| | I | 1 | − | − | 100 | 100 |
| | J | 1 | − | − | 100 | 100 |
| | K | 1 | − | − | 100 | 100 |
| | L | 1 | − | − | 100 | 100 |
| | M | 1 | − | − | 100 | 75 |
| | N | 1 | − | − | 100 | 100 |
| | O | 1 | − | − | 100 | 25 |
| | P | 1 | − | − | 100 | 100 |
| | Q | 1 | − | − | 100 | 100 |
| | R | 1 | − | − | 100 | 100 |
| | S | 1 | − | − | 100 | 100 |
| | T | 1 | − | − | 100 | 100 |
| | U | 1 | − | − | 100 | 100 |
| | V | 1 | − | − | 100 | 100 |
| Composite | U | 1 | − | − | 100 | 100 |
| Bonding | U | 1 | + | − | 100 | 100 |

Antibacterial assays were preformed using *Streptococcus mutans* as test microorganism.

In Table 1: [a]Agar Diffusion Test (ADT) —based on the diffusion of antibacterial components from the tested material into the agar. Antibacterial activity is assessed by visual inspection of inhibition zone in the bacterial lawn on the agar plates. Each experiment was performed on 8 equally prepared samples. Materials samples were aged in PBS for 24 h (A) or 30 days (A[1]) before testing. —no inhibition zone+1 mm inhibition zone++2 mm or more of inhibition zone; [b]Direct Contact Test (DCT) —Determines the antibacterial properties of insoluble materials. Following contact of ca. $10^6$ bacteria and the tested material, the presence of remaining viable bacteria are determined using a temperature-controlled spectrophotometer. Results are expressed as percent inhibition of growth. 100% inhibition=killing of all bacteria (at least $10^6$); 0% inhibition=control.

Each experiment was performed on 8 equally prepared samples. Materials samples were aged in PBS for 24 h (B) or 30 days (B[1]) before testing. The antibacterial compounds indicated in Table 1 above are those listed in Table 2 below, each characterized as indicated therein:

TABLE 2

Characteristics of the antibacterial compounds used in Table 1.

| Code | Alkyl. | Crossl | D. cross | Elemental analysis | Zeta (mV) | R (nm) |
|---|---|---|---|---|---|---|
| D PEI$_{25\,kDa}$ | $C_4$ | $C_4$ | 2% | C = 34.02<br>N = 7.93<br>I = 26.06 | 24.3 +/− 0.9 | 65 +/− 24 |
| F PEI$_{600\,kDa}$ | $C_4$ | $C_4$ | 2% | C = 32.01<br>N = 7.01<br>I = 29.65 | 47.9 +/− 2.9 | 9%: 2 +/− 1<br>17%: 22 +/− 7.5<br>74%: 400 +/− 130 |
| I PEI$_{600\,kDa}$ | $C_4$ | $C_4$ | 4% | C = 35.58<br>N = 7.7<br>I = 23.92 | 46.3 +/− 4.7 | 10%: 7.5 +/− 2.5<br>90%: 47 +/− 7.5 |
| H PEI$_{25\,kDa}$ | $C_4$ | $C_4$ | 4% | C = 24.82<br>N = 5.85<br>I = 22.51 | 45.4 +/− 0.8 | 250 |
| A PEI$_{25\,kDa}$ | $C_4$ | $C_4$ | 20% | C = 11.52<br>N = 2.11<br>I = 12.5 | 26.7 +/− 0.6 | 30 +/− 11 |
| B PEI$_{600\,kDa}$ | $C_4$ | $C_4$ | 20% | C = 24.18<br>N = 5.95<br>I = 39.03 | 42.1 +/− 1.4 | 100 +/− 36 |
| E PEI$_{25\,kDa}$ | $C_6$ | $C_5$ | 2% | C = 37.1<br>N = 5.87<br>I = 24.25 | 59.2 +/− 1.8 | 79%: 4 +/− 1.3<br>21%: 160 +/− 23 |
| G PEI$_{600\,kDa}$ | $C_6$ | $C_5$ | 2% | C = 31.16<br>N = 5.74<br>I = 34.78 | 57.2 +/− 6.4 | 165 |
| J PEI$_{25\,kDa}$ | $C_6$ | $C_5$ | 4% | C = 34.44<br>N = 6.48<br>I = 25.7 | 52.1 +/− 1.2 | 45 |
| K PEI$_{600\,kDa}$ | $C_6$ | $C_5$ | 4% | C = 33.89<br>N = 6.32<br>I = 30.5 | 66.2 +/− 1.9 | 53 +/− 19 |
| C PEI$_{600\,kDa}$ | $C_6$ | $C_5$ | 20% | C = 20.89<br>N = 3.75<br>I = 44.03 | 53.4 +/− 0.3 | 165 +/− 105 |
| T PEI$_{25\,kDa}$ | $C_8$ | $C_5$ | 2% | C = 46.36<br>N = 5.44 | — | 71%: 4.5 +/− 1<br>29%: 75 +/− 21 |
| U PEI$_{600\,kDa}$ | $C_8$ | $C_5$ | 2% | C = 44.05<br>N = 4.63 | — | 49%: 7.5 +/− 2<br>51%: 140 +/− 37 |
| L PEI$_{25\,kDa}$ | $C_8$ | $C_5$ | 2% | C = 43.47<br>N = 5.32<br>I = 22.27 | 69.2 +/− 1.4 | 120 +/− 45 |
| M PEI$_{600\,kDa}$ | $C_8$ | $C_5$ | 2% | C = 26.42<br>N = 2.95<br>I = 14.01 | 81.7 +/− 1 | 670 +/− 240 |
| Q PEI$_{25\,kDa}$ | $C_8$ | $C_5$ | 4% | | 72 +/− 2.1 | 87%: 5 +/− 1.5<br>13%: 65 +/− 23 |
| S PEI$_{600\,kDa}$ | $C_8$ | $C_5$ | 4% | C = 31.11<br>N = 3.26 | 82 +/− 0.6 | 49%: 5 +/− 1<br>51%: 265 +/− 46 |
| R PEI$_{25\,kDa}$ | $C_8$ | $C_5$ | 20% | C = 43.09<br>N = 5.82 | 66 +/− 0.2 | 84%: 5 +/− 2<br>16%: 58 +/− 16 |
| V PEI$_{600\,kDa}$ | $C_8$ | $C_5$ | 20% | C = 28.15<br>N = 4.11 | — | 53%: 7 +/− 2.5<br>47%: 157 +/− 23 |
| O PEI$_{600\,kDa}$ | $C_{10}$ | $C_5$ | 4% | C = 29.62<br>N = 3.8 | — | — |
| P PEI$_{25\,kDa}$ | $C_{10}$ | $C_5$ | 4% | C = 11.63<br>N = 1.23 | — | — |
| N PEI$_{600\,kDa}$ | $C_{10}$ | $C_5$ | 20% | C = 32.43<br>N = 4.83 | 86 +/− 0.3 | 475 +/− 155 |

PEI$_{25\,kDa}$ = polyethyleneimine of 25 kDa. PEI$_{600\,kDa}$ = polyethyleneimine of 600 kDa to 1000 kDa. Alkyl. = alkylation agent: $C_4$ = bromobutane, $C_6$ = bromohexane, $C_8$ = bromooctane, $C_{10}$ = bromodecane. Crossl. = Crosslinking agent: $C_4$ = dibromobutane, $C_5$ = dibromopentane. D. crossl. = degree of crosslinking (2%, 4% and 20% mol/mol to amine group). Elemental analysis = degree of substitution estimated by elemental microanalysis of nitrogen (% N) and carbon (% C) and (% I) using a Perkin-Elmer 2400/II CHN analyzer. Zeta = zeta measurement of the particles (Zeta potential, mV). All the particles present a positive zeta potential, which may attributed to the presence of quaternary ammonium groups of PEI on the surface. R (nm) = Particle size in nm (R = radius) determined by dynamic light scattering method using High Performance Particle Sizer (ALV-NIBS/HPPS, Langen, Germany). — = not determined yet.

Example 9

Incorporation of the 0.1-10% w/w PEI Nanoparticles into Restoration Composites is Effective Against Bacteria on Contact The purpose of this step was to examine the antibacterial activity of previously described PEI nanoparticles at various amounts (% w/w) in the dental composition on cariogenic bacteria.

A. Composition of Materials Used

The experimental specimens were prepared by adding the synthesized polymer to Filtek Flow (47% Zirconia/silica average particle size 0.01-6.0μ; BIS-GMA, TEGDMA; 3M Dental St Paul, Minn.), a commercial restorative composite resin. The addition was carried out at 0.1-10% w/w. After the polymer was added to the composite resin it was uniformly mixed with a spatula.

Preparation of the bacterial suspension, preparation of the microtiter plate, direct contact between bacteria and the tested materials, kinetic measurements of bacterial growth, data analysis and agar diffusion test were carried out as described above.

B. Results

The cationic polymeric nanoparticles with quaternary ammonium groups have been incorporated into a dental restorative composite at low concentrations (0.0001%-2%). The majority of the tested compounds was very effective by immediate contact from a concentration of 0.1% and showed complete decay of the bacteria summarized in Table 3.

TABLE 3

Effect of adding various amounts of PEI nanoparticles to dental composites on antibacterial activity.

| Antibacterial test | Content of antimicrobial compound (% w/w) | | | | | |
|---|---|---|---|---|---|---|
| | 0.1% | 0.5% | 1% | 2% | 5% | 10% |
| ADT | — | — | — | — | — | — |
| DCT | 0 | 25 | 100 | 100 | 100 | 100 |

Samples of flowable composite supplemented with various percent - % w/w - of PEI nanoparticles - (antibacterial compound coded U) were tested using ADT and DCT (for details see footnote to Table 1).

The new composites demonstrated mechanical (similar modulus and yield strength as obtained before and after incorporation of the tested nanoparticles into the restorative material) and chemical properties as the original composites but with a broad spectrum of antimicrobial activity. No leach-out of the nanoparticles was observed even upon contact of several months.

Example 10

Effect of Aging on Antibacterial Activity of Compounds Added into Dental Composite A. Preparation of the Bacteria

*Streptococcus mutans* was cultured as described above. *Enterococcus feacalis* was cultured overnight in 5 ml of brain-heart infusion broth (BHI) (Difco, Detroit, Mich., USA), at 37° C. To avoid large bacterial aggregates or long streptococcal chains, the top 4 ml of the undisturbed bacterial culture were transferred into a new test tube and centrifuged for 10 min at 3175×g. Supernatant was discarded and bacteria were resuspended in 5 ml phosphate buffered saline (PBS) (Sigma, St. Louis, Mo., USA) and vortexed gently for 10 sec. Each bacterial suspension was adjusted to an optical density 1 at 650 nm. Ten microliters from ten fold serial dilutions were plated on BHI agar to determine colony-forming units per milliliter. BHI and PBS were supplemented with streptomycin 0.005 g/ml (Sigma, St. Louis, Mo., USA) to minimize external contamination.

B. Composition of Materials Used

The experimental specimens were prepared by adding the synthesized polymer to Filtek Flow (47% Zirconia/silica average particle size 0.01-6.0μ; BIS-GMA, TEGDMA; 3M Dental St Paul, Minn.), a commercial restorative composite resin. The addition was carried out on a base of 1% w/w of two samples coded U and V. After the polymer was added to the composite resin it was uniformly mixed with a spatula.

Preparation of the microtiter plate, direct contact test between bacteria and the tested materials, kinetic measurements of bacterial growth and Data analysis were all carried out as described hereinbefore.

C. Agar Diffusion Test

*S. mutans* and *E. feacalis* were cultured as previously disclosed. 200 μl of the bacterial suspension was spread on Mitis salivarius agar (MSB) (Difco, Detroit, Mich., USA) supplemented with bacitracin 0.0625 gr/ml (Sigma, St. Louis, Mo., USA) and BHI agar supplemented with streptomycin 0.005 g/ml (Sigma, St. Louis, Mo., USA) respectively. Three light polymerized specimens of each tested material were placed on the surface. The plates were incubated for 48 h at 37° C. After the incubation the inhibition zone around each specimen was observed.

D. Material Aging

Similar microtitre plates were prepared with the tested materials and aged for 130 and 180 days. During this time each well was filled with 250 μl PBS, which was replaced every 48 h, and the plates were incubated at 37° C. Next, the PBS was aspirated and the plate was dried under sterile conditions.

E. Results

The results indicate that the alkylated polyethylenimine nanoparticles immobilized in resin-based materials have a strong antibacterial activity on both *S. mutans* and *E. feacalis* upon contact over a period of at least 180 days, as shown in Table 4 below.

TABLE 4

Effect of aging on antibacterial activity of compounds added into dental composite.

| Antibacterial compound (1% w/w) in composite | | AGING DAYS | | | | |
|---|---|---|---|---|---|---|
| | | 1 | | 30 | | 180 |
| | | ADT growth | DCT percent | ADT growth | DCT percent | ADT growth | DCT percent |
| *S. mutans* | U | — | 100 | — | 100 | — | 100 |
| | V | — | 100 | — | 100 | — | 100 |
| | Control | — | 0 | — | 0 | — | 0 |
| *E. feacalis* | U | — | 100 | — | 100 | — | 100 |
| | V | — | 100 | — | 100 | — | 100 |
| | Control | — | 0 | — | 0 | — | 0 |

Samples, 8 for each experiment, were aged in PBS for 1, 30 and 180 days before testing the antibacterial properties. Samples of composite (flowable) supplemented with 1% w/w of antibacterial compound coded U or V, were tested using ADT and DCT. Samples of composite without additives served as control. For details see footnote to Table 1.

Example 11

Effect of Antibacterial Compounds Incorporated into Dental Composite Materials on Gram Positive, Gram Negative Microorganisms and on *Candida albicans*

A. Preparation of the Bacteria

*Eschrichia coli, Staphylococcus aureus, Staphylococcus epidermidis, Pseudomonas aeroginosa, Enterococcus feacalis* and *Candida albicans* were used in the present study. Bacteria were cultured overnight in 5 ml of brain-heart infusion broth (BHI) (Difco, Detroit, Mich., USA), at 37° C. To avoid large bacterial aggregates or long streptococcal chains, the top 4 ml of the undisturbed bacterial culture were transferred into a new test tube and centrifuged for 10 min at 3175×g. Supernatant was discarded and bacteria were resuspended in 5 ml phosphate buffered saline (PBS) (Sigma, St. Louis, Mo., USA) and vortexed gently for 10 sec. Each bacterial suspension was adjusted to an optical density 1 at 650 nm. Ten microliters from ten fold serial dilutions were plated on BHI agar to determine colony-forming units per milliliter.

B. Composition of Materials Used

The experimental specimens were prepared by adding the synthesized polymer to Filtek Flow (47% Zirconia/silica average particle size 0.01-6.0μ; BIS-GMA, TEGDMA; 3M Dental St Paul, Minn.), a commercial restorative composite resin. The addition was carried out on a base of 2% w/w. After the polymer was added to the composite resin it was uniformly mixed with a spatula.

Preparation of the microtiter plate, direct contact test between bacteria and the tested materials, kinetic measurements of bacterial growth and Data analysis were all carried out as described above.

C. Agar Diffusion Test

The bacteria were prepared as previously disclosed. 200 μl of bacterial suspension was spread on BHI agar (Difco, Detroit, Mich., USA). Three light polymerized specimens of each tested material were placed on the surface. The plates were incubated for 48 h at 37° C. After the incubation the inhibition zone around each specimen was observed.

D. Results

A strong antibacterial effect of commercial polymer with the 2% w/w added synthesized polymer was observed with all bacteria tested. No growth inhibition was seen in the agar diffusion test in the Gram positive, Gram negative microorganisms and in Candida albicans as summarized in Table 5.

TABLE 5

Effect of antibacterial compounds incorporated into dental composite materials on Gram positive, Gram negative microorganisms and on *Candida albicans*.

| Bacteria | Antibacterial Compound | ADT growth inhibition | | DCT percent inhibition | |
| --- | --- | --- | --- | --- | --- |
| | | A | A[1] | B | B[1] |
| E. coli | U | — | — | 100 | 100 |
| Staph. Aureus | U | — | — | 100 | 100 |
| Staph. epidermidis | U | — | — | 100 | 100 |
| Pseudo. aeroginosa | U | — | — | 100 | 100 |
| E. faecalis | U | — | — | 100 | 100 |
| Candida albicans | U | — | — | 100 | 100 |

Samples of flowable composite supplemented with 2% w/w of antibacterial compound coded U, were tested using ADT and DCT (see footnote to Table 1 for details). Samples, 8 for each experiment, were aged in PBS for 1 (A, B,) or 7 days (A[1], B[1]) respectively, before testing their antibacterial properties using the respective test microorganisms.

Example 12

Antibacterial Activity of Alkylated Polyethylenimine Incorporated in Various Composite Resin Materials Resin composites withholding antibacterial properties may be useful in preventing recurrent caries. In this example the antibacterial effect of alkylated Polyethylenimine incorporated into bonding, flowable and hybrid composite resins was evaluated. The tests were performed on fresh samples and one week aged samples. The alkylated polyethylenimine added at 1% w/w to commercially available bonding, flowable and hybrid composite resins was copolymerized by light polymerization. The experimental samples incorporating synthesized polymer were tested for antibacterial properties both in diffusion and in direct contact. Antibacterial properties against *Streptoccocus mutans* were evaluated by 2 tests: (i) agar diffusion test and (ii) direct contact test. Statistically evident ($p<0.001$) antibacterial properties were detected only in the DCT in all three types of composite resins. The effect lasted for at least one week.

The results indicate that alkylated Polyethylenimine-type polymers synthesized in this study possess antibacterial surface properties and thus bear the potential of being immobilized into resin-based materials and be useful in reducing biofilm formation.

Resin composite restorations tend to accumulate more bacteria and dental plaque than other restorative materials in vitro and in vivo. Oral biofilm exists naturally in a healthy environment, but it is also associated with dental caries and periodontal disease. One of the bacteria frequently found in human dental plaque is *Streptococcus mutans*. *S. mutans* attaches to the surface of composite resin restorations and to the interface between the tooth and the restoration. As a result of bacterial adhesion and plaque formation secondary caries may evolve around these restorations.

The conventional method for preparing antibacterial materials is to impregnate them with antibacterial agents, such as antibiotics, silver ions, iodine and quaternary ammonium compounds, that are gradually released over time. However, such antibacterial agents tend to leach from the composite resins. Such leaching out typically results in disadvantages that may have an effect on the applicability to specific uses. Such disadvantages may be: decrease in mechanical properties of the carrier material over time, short-term effectiveness, and possible toxicity to human health if the release is not properly controlled.

The present invention, thus presents also a tool for developing antibacterial composites and coatings whose mechanism of action is not based on releasing of antiseptic agents and may thus also have application in dentistry. Antibacterial properties may extend the longevity of these restorations.

This study evaluated the antibacterial effect of synthesized alkylated polyethylenimine. This copolymeryzation resulted in a significant decrease in bacterial growth of both tested bacteria. This observation persisted at least for one week.

Tested Materials

The antibacterial effect of three composite resin materials Z250 Filtek Flow and 3M single bond adhesive supplemented with the 1% w/w of the synthesized polymer on *Streptococcus mutans* (ATCC#27351) was tested. Bacterial suspension was prepared as described above. Preparation of the microtiter plate, direct contact test between bacteria and the tested materials, kinetic measurements of bacterial growth and data analysis and agar diffusion test were all carried out as described above.

Figure 9:
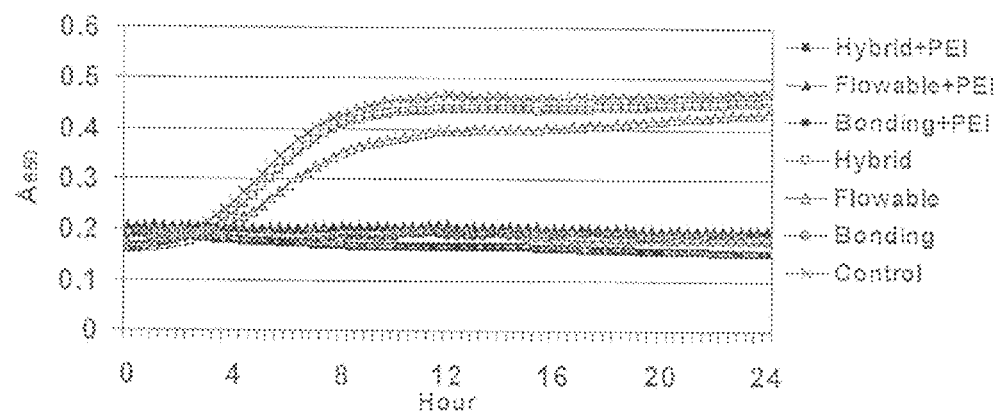
FIG. 9 depicts the average optical density measurements of 7 wells of Streptococcus mutans growth following immediate direct contact with various composite resin materials (Z250=Hybrid; Filtek Flow=Flowable and 3M single bond adhesive=Bonding) incorporated with PEI nanoparticles (relative to control—the commercial composite resin; bacterial growth with no composites=Co+).
Figure 10:
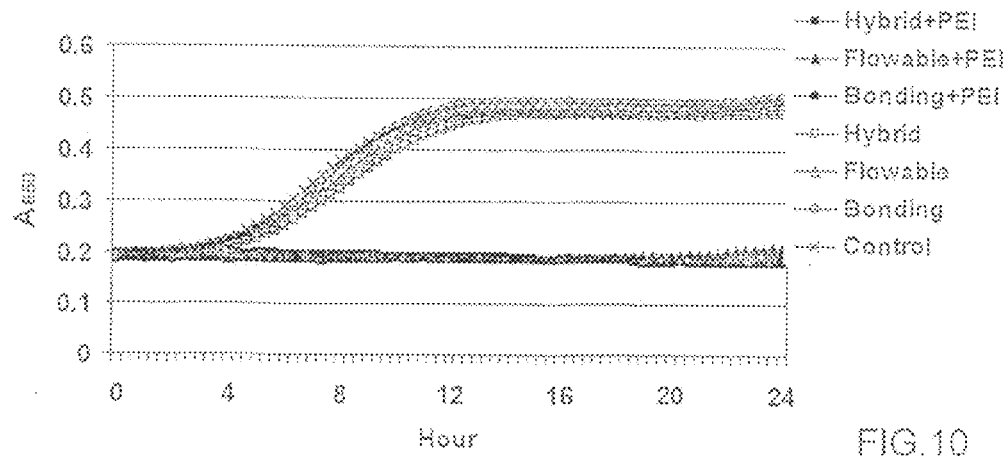
FIG. 10 depicts the same experiment as in FIG. 9 conducted after an aging process of 1 month.

Average optical densities measurements of 7 wells of *Streptococcus mutans* growth following immediate direct contact with the tested materials during a 24 hr experiments are shown in FIG. 9. This figure compares the antibacterial effect of the three commercial materials with and without the added polymer in direct contact with *streptococcus mutans*. A strong antibacterial effect is seen in all three types of commercial polymers with the added synthesized polymer. FIG. 10 depicts the same experiment conducted after an aging process of 1 week. After a 1 week aging process the antibacterial effect of the commercial composite resins with the added polymer was kept.

In the agar diffusion test no inhibition zone was detected in all tested samples.

The calibration results were found to be reproducible shown in FIG. 11. Gradual decrease of the optical density was in correlation to the serial dilutions. As seen in the calibration results the DCT system had no effect on the bacterial growth rate or the final optical density of the stationary phase.

For composite resin restorations incorporation of polymers into the materials scaffold, may solve the ending effect of slow released agents and prolong significantly the antibacterial properties. The inhibitory antibacterial effect of incorporated alkylated polyethylenimine was probably due to the direct contact with the tested bacteria, and not due to the polymer release, because they were insoluble in the culture media, and there was no release of the synthesized polymer from the composites. Although the detailed mechanism of the antibacterial effect of these materials has not been determined, it is hereby suggested without being bound to any possible theory that quaternary ammonium compounds cause lysis of the bacterial cells by binding to the cell wall components and causing leakage of the cytoplasmatic material. The synthesized polymer exhibited a strong antibacterial effect against the two tested bacteria with no regard to the commercial composite resin it was added to. This effect persisted for at least a week.

Example 13

Demonstrating that the Antibacterial Activity is a Surface Phenomenon Expressed Only by Direct Contact of the Bacteria with the Material In order to eliminate the possibility that the antimicrobial activity is due to bioactive components that were released to the medium, three tests were performed: (A) the agar diffusion test—ADT, (B) antimicrobial effect of the medium the composites were immersed in, and (C) chemical analysis of the medium.

Agar Diffusion Test (ADT)—

A semi-quantitative test based on the diffusion of antibacterial components from the tested material and the visual inspection of inhibition zone in the bacterial lawn grown oil agar plates.

The antibacterial properties of the eluted components released from the tested materials were evaluated. The bacterial growth curves of *S. mutans* were similar to that of the appropriate control for the 1% w/w and 5% added nanoparticles. Experiments repeated for with the one week aged samples before performing the test of eluted components yielded similar results.

UV and GPC analysis of the medium in which the composites were immersed showed no organic molecules or polymers.

*Streptococcus mutans* (ATCC #27351) bacterial suspension and the agar diffusion tests were carried out as described above.

A. Preparation of the Microtiter Plate

Three composite resin materials Z250 Filtek Flow and 3M single bond adhesive supplemented with the 1% w/w and 5% w/w of the synthesized polymer were tested. Using a flat-ended dental instrument (dental spatula) the sidewalls of 7 wells in a microtiter plate (96-wells flat bottom Nunclon, Nonc, Copenhagen, Denmark) were coated evenly with an equal amount of the same tested. Special care was taken to leave the bottom of the well untouched in order to avoid false readings during the incubation in the spectrophotometer. The materials were polymerized according to the manufacturers' instructions. Seven wells in the same microtiter plate without the tested material, and 7 additional wells coated with the commercial composite resins with no synthesized polymer served as a positive control.

B. Dissolution Behavior

Each well was supplemented with 230 µl of BHI and incubated for 24 hrs at 37° C. A 220 µl volume from each well was transferred to an adjacent set of wells and 10 µl of a bacterial inoculums prepared as described above, were added, thus testing the effect of components eluted into the broth. The plate was placed in the temperature-controlled microplate spectrophotometer, set at 37° C., with 5 sec mixing before each reading. Bacterial growth was assessed by following the changes in $OD_{650}$ every 20 min for 24 hrs.

Similar microtitre plates were prepared with the tested materials and aged for 1 and 4 weeks. During this time each well was filled with 250 µl PBS, which was replaced every 48 h, and the plates were incubated at 37° C. In the final 24 hrs the PBS was replaced with BHI broth and the same test as for the immediate samples was performed. In a complementary experiment, the composites were immersed in deionized water 102 mg composite in 1 ml of water at 37° C. for one, and 7 days and the solutions were concentrated by lyophilization. Tests for released molecules in the water were carried out by UV scan between 200 and 600 nanometer and by GPC-Spectra Physics instrument (Darmstadt, Germany) containing a pump, column (Shodex KB-803) and refractive index (RI) detector, 0.05M $NaNO_3$ as eluent at 1 ml/min.

The direct contact test between bacteria and the tested materials, kinetic measurements of bacterial growth and data analysis were all carried out as described above.

The antibacterial properties of the eluted components released from the tested materials were evaluated. In the agar diffusion test no inhibition zone was detected in all tested samples. The bacterial growth curves of *S. mutans* were similar to those of the appropriate control for the 1% and 5% w/w added nanoparticles, both for immediately prepared samples (Table 4) and in the one week and 4 weeks aged samples. Both Filtek Flow and Single Bond Adhesive decreased bacterial growth in the non-aged samples, which did not last for more than a one week period.

Furthermore, UV and GPC analysis of the medium in which the composites were immersed, showed no organic molecules or polymers. The results are presented in Table 6.

TABLE 6

Possible antimicrobial effect of leachable extracts from composites.

| Tested material | Content of antimicrobial compound (wt %) | ADT | Inhibition of growth in elute | UV analysis | GPC analysis |
|---|---|---|---|---|---|
| Hybrid composite | 1 | — | 0 | — | — |
|  | 5 | — | 0 | — | — |
| Flowable | 1 | — | 0 | — | — |
|  | 5 | — | 0 | — | — |
| Bonding | 1 | — | 0 | — | — |
|  | 5 | — | 0 | — | — |

The agar diffusion test was performed as described in the footnote to Table 1. Inhibition of bacterial growth - This test quantitatively evaluated the bacterial growth in the elute of the composite resin materials supplemented with various degrees of PEI nanoparticles sample coded U (w/w). Results are in percent inhibition of the bacterial growth. This assay tested aged samples (1 and 7 days). UV and GPC analysis- no traces of organic molecules or polymers These experiments indicate that the bioactivity of these composites is not through the release of compounds to the medium from the composite and the activity is associated with surface contact.

Example 14

Formation of Quaternary Ammonium by Reductive Amination

While direct alkylation of a polyamine with long chain alkyl halide followed by methylation with methyl halide may provide quaternary ammonium groups, the alkylation is random and more than one long chain alkyl may attach to an amino group. An alternative method for a controlled quaternarization of a polyamine is by first attaching the long chain alkyl groups to primary amines by reductive amination. In this process, a polyamine such as branched polyethylene imine having in average of 25% primary amines is reacted with an alkanal having a chain of 4-15 carbons to form the corresponding imine derivative only with the primary amines. The imines are then reduced to the corresponding secondary amines. In the following step, the secondary amines and tertiary amines are alkylated with excess methyl halide to form the corresponding quaternary amines. This method resulted in a reproducible quaternized polyamine.

Example 15

Replacing the Halide Group with Hydroxy Counter Ions

The resulted quaternary amine polymers having chloro or iodo counter ion is reacted with AgO under basic conditions where AgCl or AgI is formed and precipitated from the solution forming the OH— ammonium derivative. The hydroxyl groups can be then converted into the fluoro ions by reacting the particles with a solution of HF.

Example 16

Polysaccharide Quaternary Ammonium Particles

Quaternary ammonium salts of soluble or insoluble particulate polysaccharides was achieved by either oxidation of the polysaccharide to form the polyaldehyde which in the subsequent step reacted with an oligoamine derivative having at least two amino groups with one of them being a primary amine that is conjugated to the oxidized polysaccharide by reductive amination and the other amine being a quaternary amine with long alkyl chain for antimicrobial activity or an amine that is converted into a bioreactive quaternary ammonium groups prepared by alkylation as described in the previous examples.

Example 17

Activity After 6 Months of Aging

FIG. 12 shows a full antibacterial activity after 6 months of ageing of restorative samples loaded with 1% w/w of crosslinked PEI-quaternary ammonium.

Example 18

Cationic Polysaccharide Paprticles

A range of polyethyleneimine (PEI, MW=600), spermine and spermidine conjugated to arabinogalactan (AG, a branched polysaccharide, MW=25,000) dextran (Dex, a linear 1,6-polyglucose, MW=30,000) or pullulan (Pul, a linear 1,4 polyglucoser, MW=50,000) were prepared. The oligoamines were conjugated by an amine or imine bond after oxidation of the polysaccharide into a polyaldehyde. The difference between the polymers tested for biological activity were: 1. the oligoamine used, either PEI, spermine or spermidine; 2. the type of polysaccharide, AG, pullulan or Dex; 3. the type of bond, amine or imine; and 4. the content of oligoamine per saccharide unit Abbreviations used herein are: -AG (1:1): oxidized Arabinogalactan produced by reacting 1 mole of saccharides units and 1 mole of periodate (35% of saccharides units were converted to di-aldehydes); -AG (1:5): oxidized Arabinogalactan produced by reacting 1 mole of saccharides units and 0.2 mole of periodate (8% of saccharides were converted to di-aldehydes); -D (1:1): oxidized Dextran produced by reacting 1 mole of saccharides and 1 mole of periodate (50% of saccharide units were converted to di-aldehydes); -P (1:1): oxidized pullulan produced by reacting 1 mole of saccharides units and 1 mole of periodate (degree of oxidation was not determined); -PEI: Polyethylene imine (Mw=600); -Red: Reduced conjugates (amine bonds); -Unred: Unreduced conjugates (imine bonds).

Example 19

Synthesis of Cationic Polysaccharide Conjugates

Polysaccharide-PEI crosslinked conjugates were prepared by reductive amination. Polysaccharides were oxidized by the reaction of the polysacchariude with an oxidizing agent such as periodate. The oxidized polysaccharide was then reacted with an oligoamine under concentrated solution to induce crosslinking. In a typical experiment, 0.5 g. of oxidized Arabinogalactan (1:5, ~0.5 mmoles of aldehydes) and 0.18 g. of PEI (0.625 mmol) were dissolved in 2 ml borate buffer (0.1M, pH=11). The solution was mixed at room temperature for 48 h. Half of the solution (10 ml) was dialyzed against DDW using 12,000 cut-off cellulose tubing and lyophilized to obtain the imine conjugate which was insoluble in water. The other half was reacted with excess sodium borohydride at room temperature over-night, dialyzed against DDW and lyophilized to obtain the amine conjugate which was soluble in water.

Aldehyde/PEI (1:1.25, mole ratio): Dextran and Pullulan conjugates were prepared similarly by replacing AG with the corresponding polysaccharide. Also, spermine, spermidine and other oligoamines were conjugated to various polysaccharides using this process. The oligoamine conjugates were quaternized using the methods described above for chitosan and polyethylene imine. In one experiment, the oligoamine-polysaccharide conjugate was reacted with 1-bromo-octane and subsequently with methyl bromide to obtain the desired quaternary ammonium particles. The particles were highly effective in killing bacteria.

Example 20

Quaternary Ammonium Methyl Styrene Based Antimicrobial Resins

A. Alkylation Poly(Styrenemethylamine) with Bromooctane:

N-Alkylation was carried out as follows: crosslinked poly(styrenemethylamine) (10 g, 74.5 mmol of monomer units) dispersed in 100 ml of absolute ethanol was reacted with excess of bromooctane (110 mmol, 19.3 ml) at 1:1.5 mole ratio (poly(styrenemethylamine) unit/bromooctane). The alkylation step was carried out under reflux conditions for 24 hours. Excess of NaOH (2 equimolar), dissolved in the minimum amount of methanol was added to neutralize released HBr. Neutralization reaction was continued for additional 24 hours at the same conditions. After cooling to room temperature, obtained product was filtered off, washed with acetone and DDW to remove traces of bromooctane and NaBr, respectively and vacuum-dried over $P_2O_5$. Alternatively, monoalkylation onto aminomethylated groups was achieved by reductive amination with alkanals having 4 or longer carbon chain. Elemental analysis: C(%)=58.32, H(%)=7.79, N(%)=4.01, Br(%)=20.78.

B. Methylation of the Octane Alkylated Poly(Styrenemethylamine)

Previously alkylated poly(styrenemethylamine) (2.01 g, 8.1 mmol of monomer units) dispersed in 20 ml of absolute ethanol was reacted with 1.27 ml of methyl at 1:2.5 mole ratio (monomer unit/methyl iodide). Methylation step was continued for 48 hours at 600 C. An equimolar amount of sodium bicarbonate (0.02 mol, 2 g) was added to collect released HI during methylation step. Neutralization was continued at the same conditions for additional 24 hours. Obtained product was discarded by filtration and washed with acetone and DDW to remove traces of the methyl iodide and sodium bicarbonate, respectively and vacuum-dried over $P_2O_5$. Elemental analysis: C(%)=54.85, H(%)=6.77, N(%)=3.50, I(%)=31.14.

C. Preparation of Chitosan Nanoparticles

Nanoparticles were spontaneously obtained upon addition of tripolyphosphate aqueous solution to the chitosan solution. Chitosan was dissolved in 0.05% (w/v) acetic acid solution at a concentration of 0.25% and the pH adjusted to 5.5 with a 0.5% (w/v) NaOH solution. Tripolyphosphate was dissolved in purified water at a concentration of 0.2% (w/v). Following this, 0.8 ml of the tripolyphosphate solution was added to 2.5 ml of the chitosan solution, thereby leading to the formation of the nanoparticles. The final pH of the nanoparticles suspension was 6.4. Different mean size of nanoparticles were obtained by adjusting the ratio of chitosan and tripolyphosphate.

D. Alkylation of Chitosan with Various Alkyl Bromides 2 g of chitosan was added into 40 mL of 2-propanol/4 N sodium hydroxide solution and stirred at 70° C. for 30 min. The alkyl bromide from butyl bromide, octyl bromide, dodecyl bromide, and hexadecyl bromide were added dropwise to the mixture and allowed to react for 4 h, and then the reaction mixture was centrifuged. The obtained precipitate was washed with ethanol and then dried at vacuum to obtain the alkylated chitosan derivatives. The resultant alkylated chitosan derivatives were dialyzed for 3 days using Cellu SepH1 membrane (MWCO=12 000) against water. The degree of substitution was determined by potentiometric titration.

The invention claimed is:

1. A polymeric particle, comprising:
at least one aliphatic polymer; and
anti-microbially active quaternary ammonium groups chemically bound to the at least one aliphatic polymer at a surface density of at least one anti-microbially active quaternary ammonium group per sq. nm.;
the nitrogen atom of each quaternary ammonium group having
at least one bond to the aliphatic polymer,
one and no more than one bond to an alkyl group having from 4 to 10 carbon atoms, and
a remainder of bonds each being to a non-polymeric group.

2. The polymeric particle according to claim 1, wherein the non-polymeric group is an alkyl group having from 1 to 3 carbon atoms.

3. The polymeric particle according to claim 1, wherein the nitrogen atom of each quaternary ammonium group has one or two bonds to the aliphatic polymer.

4. The polymeric particle according to claim 1, wherein the at least one aliphatic polymer is selected from the group consisting of polyethylene imine, polyvinyl amine, poly(allyl amine), poly(aminoethyl acrylate), aminomethylated styrene polymers, polypeptides with pending alkyl-amino groups, and chitosan.

5. The polymeric particle according to claim 1, having a size of from 10 to 10,000 nm.

6. The polymeric particle according to claim 5, having a size of from 10 to 150 nm.

7. The polymeric particle according to claim 5, having a size of from 30 nm to 1000 nm.

8. The polymeric particle according to claim 1, wherein the at least one aliphatic polymer is cross-linked with a cross-linking agent.

9. The polymeric particle according to claim 8, wherein the degree of cross-linking is from 1% to 20%.

10. The polymeric particle according to claim 8, further comprising quaternary ammonium groups
wherein each nitrogen of each quaternary ammonium group has
from one to two bonds to the aliphatic polymer,
one and no more than one bond to an alkyl group having from 4 to 10 carbon atoms,
one bond to the cross-linking agent, and
optionally remaining bonds each being to an alkyl group having from 1 to 3 carbon atoms.

11. The polymeric particle according to claim 1, wherein the alkyl group having from 4 to 10 carbon atom is an alkyl group having 6, 7, or 8 carbon atoms.

12. The polymeric particle according to claim 2, wherein the alkyl group having from 1 to 3 carbon atoms is a methyl group.

13. The polymeric particle according to claim 1, wherein a quaternary ammonium group is counter-balanced with a fluoride anion.

14. The polymeric particle according to claim 1, wherein at least 10% of the amine groups in the polymer are the anti-microbially active quaternary ammonium groups.

15. The polymeric particle according to claim 1, having functional groups that are capable of reacting with a host polymer or with monomers thereof, to allow the particles to be bound chemically to the host polymer.

16. The polymeric particle according to claim 1, embedded in a liquid or solid medium.

17. The polymeric particle according to claim 16, wherein the medium is a polymeric matrix.

18. The polymeric particle according to claim 17, which is homogeneously distributed on the outer surface of said polymeric matrix at a surface concentration of at least about one particle per 1 sq. μm.

19. A composition comprising the polymeric particle according to claim 1.

20. The composition according to claim 19, wherein the composition is a pharmaceutical composition.

21. A polymeric matrix comprising the polymeric particles according to claim 1.

22. The polymeric matrix according to claim 21, wherein the polymeric particles are homogeneously distributed on the outer surface of the matrix in a surface concentration of between about 1 to about 100 particles per sq. μm.

23. The polymeric matrix according to claim 21, wherein the polymeric particles are homogeneously distributed on the outer surface of said polymeric matrix at a surface concentration from about 1 to about 10 particles per sq. μm.

24. The polymeric matrix according to claim 21, having, on the average, at least one active particle per sq. μm of outer surface of the matrix, the size of such particle being at least 100 nm$^2$.

25. The polymeric matrix according to claim 21, wherein the polymeric particles are chemically bound to the polymeric matrix.

26. The polymeric matrix according to claim 21, further comprising a strong reducing agent or a strong oxidizing agent.

27. A method for inhibition of biological species, comprising contacting the biological species with a polymeric matrix according to claim 21.

28. The method according to claim 27, affecting annihilation of at least 95% of the contacted biological species.

29. The method according to claim 28, affecting annihilation of at least 99% of the contacted biological species.

30. The method according to claim 27, wherein the biological species is selected from the group consisting of bacteria, parasites, fungi, and viruses.

31. The method according to claim 27, wherein the polymeric matrix contains at most 5% w/w polymeric particles.

32. A method for obtaining a polymeric matrix comprising polymeric host embedding particles, the method comprising adding to a host polymer a surface active compound and particles according to claim 1, and mixing to obtain a homogenous polymeric matrix, wherein the polymeric particles are homogeneously distributed on the outer surface of the matrix in a surface concentration of at least about 1 particle per sq. μm.

33. A method for obtaining a polymeric matrix comprising polymeric host embedding particles, comprising mixing a host polymer with a compatibilizer, and then with particles according to claim 1, wherein the polymeric particles are homogeneously distributed on the outer surface of the matrix in a surface concentration of about 1 particle per sq. μm.

34. The method according to claim 33, wherein the compatibilizer is selected from the group consisting of monomers of the hosting polymer, monomers of the polymer from which the particle is made, oligomers of monomers of the hosting polymer, oligomers of monomers of the particle's polymer, and oligomers made of monomers of both kinds.

35. A method for obtaining a polymeric matrix according to claim 21, further comprising polymerizing host monomers in the presence of the polymeric particles.

36. A method for inhibiting or preventing the growth of a biological species on a medical appliance, comprising applying onto said medical appliance a pharmaceutical composition comprising polymeric particles according to claim 1, or a matrix comprising a polymeric host embedding the particles.

37. The method according to claim 36, wherein the medical appliance is selected from the group consisting of a bone cement, a joint, a lens, a stent, an artificial heart valve, an artificial skin, an implant, an intra uterine device, a neurosurgical shunt, a urethral stent, a coating for a subcutaneous insulin pump, a coating for a subcutaneous contraceptive, a coating for a subcutaneous pacemaker, a tubing or a canulla used for intra venous infusion, a tubing or canulla used for dialysis, a surgical drainage tubing, a urinary catheter, an endotracheal tube, a wound covering material, a suture, a catheter for use in blood vessels or the urinary system, a shunt for use in brain applications, a surgical glove, a tip for ear examination, a stethoscope end, a dental adhesive, a dental restorative composite based material for filling tooth, decay cavities, a dental restorative endodontic filling material for filling the root canal space in root canal treatment, a dental restorative material used for provisional and final tooth restorations or tooth replacement, a dental inlay, a dental onlay, a crown, a partial denture, a dental implant, a plastic wear for medical and research laboratories, food packaging, and a paint.

38. The method according to claim 37, wherein the medical appliance is a dental restorative material.

39. The method according to claim 37, wherein the medical appliance is bone cement.

40. The method according to claim 37, wherein the medical device is a joint.

41. The method according to claim 37, wherein the medical appliance is a lens.

42. The method according to claim 37, wherein the medical appliance is a stent.

43. The method according to claim 37, wherein the medical appliance is a wound covering material.

44. The method according to claim 37, wherein the medical appliance is a catheter for use in blood vessels or the urinary system.

45. A method according to claim 36, wherein the inhibition of biological species activity does not leach out and remains active for longer than 6 months.

* * * * *